US010007756B2

(12) United States Patent
Kuo

(10) Patent No.: US 10,007,756 B2
(45) Date of Patent: Jun. 26, 2018

(54) MEDICAL IMAGING SYSTEM FOR SCAN QUEUE MANAGEMENT

(71) Applicant: Yu-Ching Audrey Kuo, Toronto (CA)

(72) Inventor: Yu-Ching Audrey Kuo, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 95 days.

(21) Appl. No.: 15/108,342

(22) PCT Filed: Apr. 13, 2015

(86) PCT No.: PCT/IB2015/052677
§ 371 (c)(1),
(2) Date: Jun. 27, 2016

(87) PCT Pub. No.: WO2016/166569
PCT Pub. Date: Oct. 20, 2016

(65) Prior Publication Data
US 2017/0046482 A1    Feb. 16, 2017

(51) Int. Cl.
*G06K 9/00* (2006.01)
*G06F 19/00* (2018.01)
(Continued)

(52) U.S. Cl.
CPC ............. *G06F 19/321* (2013.01); *A61B 5/00* (2013.01); *A61B 5/055* (2013.01); *A61B 6/54* (2013.01);
(Continued)

(58) Field of Classification Search
None
See application file for complete search history.

(56) References Cited

U.S. PATENT DOCUMENTS 6,522,713 B1    2/2003  Valiga et al.
6,678,703 B2    1/2004  Rothschild et al.
(Continued)

OTHER PUBLICATIONS

Atkinson, Dennis. "International Search Report" for PCT International Application No. PCT/IB2015/052677 dated Jan. 8, 2016.
(Continued)

*Primary Examiner* — Idowu O Osifade
(74) *Attorney, Agent, or Firm* — Perry + Currier Inc.

(57) ABSTRACT

A medical imaging system for scan queue management is provided, comprising: a computing device; a display device; and, an imaging device; the computing device configured to: render: a graphical scan queue comprising a first graphical representation of a type of each respective digital image series of a plurality of digital image series, in an order corresponding to an order in which the series are to be acquired; and, a graphical indication of respective total estimated times for acquiring each of the series; render, at the display, a respective graphical timer on each respective first graphical representation as the series are acquired, the respective graphical timer indicating acquisition progress; receive, from the imaging device, the respective series as they are acquired; store the respective series; and, when acquisition of the respective series occurs, render a graphical indicator of a next respective series to be acquired in the scan queue.

13 Claims, 19 Drawing Sheets

(51) Int. Cl.
    *A61B 5/00*     (2006.01)
    *A61B 5/055*     (2006.01)
    *G01T 1/164*     (2006.01)
    *G06T 11/00*     (2006.01)
    *G16H 40/63*     (2018.01)
    *G01R 33/54*     (2006.01)
    *G01R 33/56*     (2006.01)
    *A61B 6/03*     (2006.01)
    *A61B 6/00*     (2006.01)

(52) U.S. Cl.
    CPC ............ G01R 33/546 (2013.01); G01T 1/164 (2013.01); G06F 19/3406 (2013.01); G06T 11/00 (2013.01); G16H 40/63 (2018.01); *A61B 6/032* (2013.01); *A61B 6/037* (2013.01); *A61B 6/461* (2013.01); *A61B 6/467* (2013.01); *G01R 33/543* (2013.01); *G01R 33/5601* (2013.01); *G01R 33/5602* (2013.01); *G06T 2207/10081* (2013.01); *G06T 2207/10088* (2013.01); *G06T 2207/10101* (2013.01); *G06T 2207/10104* (2013.01); *G06T 2210/41* (2013.01)

(56) References Cited

U.S. PATENT DOCUMENTS

| | | |
|---|---|---|
| 2002/0175910 A1 | 11/2002 | Toda |
| 2012/0089011 A1 | 4/2012 | Wang et al. |
| 2014/0292330 A1* | 10/2014 | Gulani ............... G01R 33/3614 324/309 |
| 2016/0163047 A1* | 6/2016 | Oh ....................... G01R 33/543 382/131 |

OTHER PUBLICATIONS

International Preliminary Report on Patentability dated Oct. 17, 2017, by ISA, re PCT International Patent Application No. PCT/IB2015/052677.

* cited by examiner

MEDICAL IMAGING SYSTEM FOR SCAN QUEUE MANAGEMENT

FIELD

The specification relates generally to medical imaging, and, in particular, a medical imaging system for scan queue management.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures, and blood vessels when used in conjunction with an intra-venous agent such as an iodinated contrast agent. Vascular visualization may also be acquired by MRI using a contrast agent, such as an intra-venous gadolinium based contrast agent which has pharmaco-kinetic properties that enable visualization of tumors (in some instances), and break-down of the blood brain barrier. These multi-modality solutions can provide varying degrees of contrast between different tissue types, tissue function, and disease states. Imaging modalities can be used in isolation, or in combination to better differentiate and diagnose disease.

In some instances contrast agents may be used to emphasize certain anatomical regions during imaging. For example, a Gadolinium chelate injected into a blood vessel will produce enhancement of the vascular system, or the presence and distribution of leaky blood vessels. Iron-loaded stem cells injected into the body and defected by MRI will allow stem cell migration and implantation in-vivo to be tracked. For a contrast agent to be effective the contrast agent must preferentially enhance one tissue type or organ over another. Furthermore, the preferential augmentation of signal must be specific to the particular tissue type or cell of interest.

All contrast agents will shorten the MRI T1 and T2 relaxation times of nearby tissue; however, it is useful to subdivide them into two main groups. T1 contrast agents, or "positive" agents, decrease T1 approximately the same amount as T2, these agents typically give rise to increases in signal intensity in images. Examples of T1 agents are paramagnetic gadolinium- and manganese-based agents. The second group can be classified as T2 contrast agents, or "negative" agents, these agents decrease T2 much more than T1 and hence typically result in a reduction of signal intensity in images. Examples of T2 contrast agents are ferromagnetic and superparamagnetic iron oxide based particles, commonly referred to as superparamagnetic iron oxide (SPIO) and ultra-small superparamagnetic iron oxide (USPIO) particles. Furthermore, quantitative evaluation of contrast uptake can be used to evaluate blood-brain barrier disruptions and/or angiogenesis of tumors; hence, timing of contrast injection can be important in these instances.

Contrast agents can further be classified as targeted or non-targeted. A targeted contrast agent has the ability to bind to specific molecules of interest. In some cases, the T1 relaxation time of the agent significantly decreases upon binding. For example, MS-325 is an agent that binds to serum albumin in the blood. For many agents (including MS-325), the T1 relaxation time of the agent in the bound state is a strong function of the magnetic field strength. When this is the case (i.e. a molecule's T1 relaxation time is a strong function of the magnetic field strength), the molecule is said to have T1 dispersion.

Scan queue management is a particular issue when acquiring digital images with medical imaging devices, particularly in light of contrast agent introduction. For example, in an imaging study, scan queues typically consists of several series protocols. Each series protocol often consists of instructions for scanning and instructions for reconstructing the scanned images. Typically, one series protocol produces one series of images. However, with the advent of more sophisticated imaging techniques, several types of reconstruction algorithms may be applied in order to extract different information from the same data to address different clinical or research concerns. In other words, there could be multiple series of images that are derived from the same original imaging data. Traditional graphical user interfaces can be confusing as reconciliation of the scan instructions with the scanned images occurs either by knowledge of a nature of a scan and/or by understanding a naming convention of the image series.

In addition to having multiple derived image series associated with one series protocol, some imaging technique may also have a time-resolved feature where the same set of scanning instructions is repeated multiple times. In the context of MR imaging, for example, some scanners group all repeated scans in the same series while others consider each repeat as a separate series.

A time-resolved feature often requires intervention between the repeating scans. An interface first provides an alert that intervention is required, such as administering image contrast enhancing agent. The timing from such interventions to subsequent repeated scans can be crucial but can often be mismanaged due to complicated interfaces and confusing trigger instructions.

Another common confusion often occurs as a result of inconspicuous display of scan queue status. It may not be easy to discern if a series scan has started, paused but later restarted if a series protocol is currently undergoing scanning process or editing process.

Furthermore, image post-processing is often performed without feedback. Image post-processing is often time-consuming. The progress of image post-processing is often inferred by counting the number of images in an image series or after double-checking an image selection list. The long wait for feedback can be frustrating, as subsequent tasks that are to be performed after feedback (such as reviewing study completeness and/or sending images to an archival server) are delayed.

SUMMARY

The present specification is directed to a medical imaging system for scan queue management in which a computing device coordinates scanning using an imaging device with rendering of a scan queue at a display device. Graphical indications of each scan in a scan queue are provided in an order at the display device which corresponds to a scan order in a scan prescription. The graphical indications are updated as respective scans occur at the imaging device to show an indication of type of scan before a scan occurs, a timer and/or an acquisition progress indicator for a respective scan as the scan is occurring and, optionally, an indication of digital images acquired during the scan after the scan has occurred. The graphical indications are provided in conjunction with a timer showing a total time and/or a total estimated time, for implementing the scan prescription, in addition to the individual timers for each of the scans. When a scan that is occurring includes a pause for contrast agent injection, the associated timer for the graphical indication is configured to show the pause. When estimated processing time is available, a time and/or progress status of data processing may be also provided.

An aspect of the specification provides a medical imaging system for scan queue image management, the medical imaging system comprising: a computing device comprising a processor, a communication interface and a memory; a display device; and an imaging device configured to acquire digital images, the computing device configured to communicate with the display device and the imaging device using the communication interface, communication with the imaging device occurring for a duration of a scan queue series, the processor configured to: generate a scan prescription comprising instructions for causing the imaging device to acquire a plurality of digital image series, each of the plurality of digital image series comprising a respective series of digital images; render, at the display device: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series; transmit, using the communication interface, the scan prescription to the imaging device; render, at the display device, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated; receive, from the imaging device, using the communication interface, the respective digital image series as the respective digital image series are acquired; store, at the memory, the respective digital image series; and, when acquisition of the respective digital image series has occurred, render, at the display device, a graphical indicator of a next respective digital image series to be acquired in the graphical scan queue.

The processor may be further configured to, when acquisition of the respective digital image series has occurred, replace the first graphical representation in the graphical scan queue with an updated graphical representation indicative of the respective digital image series that was acquired.

The processor may be further configured to, when acquisition of the respective digital image series has occurred, remove the respective graphical timer from the respective first graphical representation.

The processor may be further configured to, render, at the display device, estimated times to acquire the respective graphical image series on each of respective first graphical representations prior to each of the respective digital image series being acquired.

The processor may be further configured to, when acquisition of the respective digital image series has occurred, render at least a portion of the respective digital image series in an information area adjacent the graphical scan queue.

The processor may be further configured to: render, at the display device, an information area adjacent the graphical scan queue: and render contextual operational information in the information area according to a mode in which the medical imaging system is currently operating.

The processor may be further configured to control the computing device and the imaging device to operate in one or more modes, the one or more modes including one or more of: a setup mode wherein the scan prescription is generated; a scan mode wherein the plurality of digital image series is acquired; and a view mode wherein the plurality of digital image series are rendered at the display device.

The imaging device may be further configured to pause when acquiring the respective series of digital images to allow for injection of a contrast agent into an area being imaged, and the processor may be further configured to insert a pause indication into the respective graphical timer corresponding to the pause in acquiring the respective series of digital images.

The processor may be further configured to render each respective first graphical representation rendered in the graphical scan queue in an order by rendering each respective first graphical representation rendered in the graphical scan queue side-by-side with each other.

The first graphical representation may comprise a textual indication of a type of scan associated with an operational mode of the imaging device when acquiring the respective digital image series.

The imaging device may comprise a magnetic resonance imaging (MRI) device.

The imaging device may comprise one or more of: a magnetic resonance imaging (MRI) device, an Optical Coherence Tomography (OCT) device a computerized tomography (CT) device, a computerized axial tomography (CAT) device, and a positron emission tomography (PET).

Another aspect of the specification provides a method for scan queue management comprising: at a medical imaging system comprising: a computing device comprising a processor, a communication interface and a memory; a display device; and, an imaging device configured to acquire digital images, the computing device configured to communicate with the display device and the imaging device using the communication interface, communication with the imaging device occurring; for a duration of a scan queue series: generating, at the processor, a scan prescription comprising instructions for causing the imaging device to acquire a plurality of digital image series, each of the plurality of digital image series comprising a respective series of digital images; rendering, at the display device: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series; transmitting, using the communication interface, the scan prescription to the imaging device; rendering, at the display device, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated; receiving, from the imaging device, using the communication interface, the respective digital image series as the respective digital image series are acquired; storing, at the memory, the respective digital image series; and, when acquisition of the respective digital image series has occurred, rendering, at the display device, a graphical indicator of a next respective digital image series to be acquired in the graphical scan queue.

Yet a further aspect of the specification provides a computer-readable medium storing a computer program, wherein execution of the computer program is for: at a medical imaging system comprising: a computing device comprising a processor, a communication interface and a memory; a display device; and, an imaging device configured to acquire digital images, the computing device configured to communicate with the display device and the imaging device using the communication interface, communication with the imaging device occurring for a duration of a scan queue series: generating, at the processor, a scan prescription comprising instructions for causing the imaging device to acquire a plurality of digital image series, each of the plurality of digital image series comprising a respective series of digital images; rendering, at the display device: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series; transmitting, using the communication interface, the scan prescription to the imaging device; rendering, at the display device, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated; receiving, from the imaging device, using the communication interface, the respective digital image series as the respective digital image series are acquired; storing, at the memory, the respective digital image series; and, when acquisition of the respective digital image series has occurred, rendering, at the display device, a graphical indicator of a next respective digital image series to be acquired in the graphical scan queue. The computer-readable medium may comprise a non-transitory computer-readable medium.

BRIEF DESCRIPTIONS OF THE DRAWINGS

Embodiments will now be described, by way of example only, with reference to the drawings, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Figure 1:
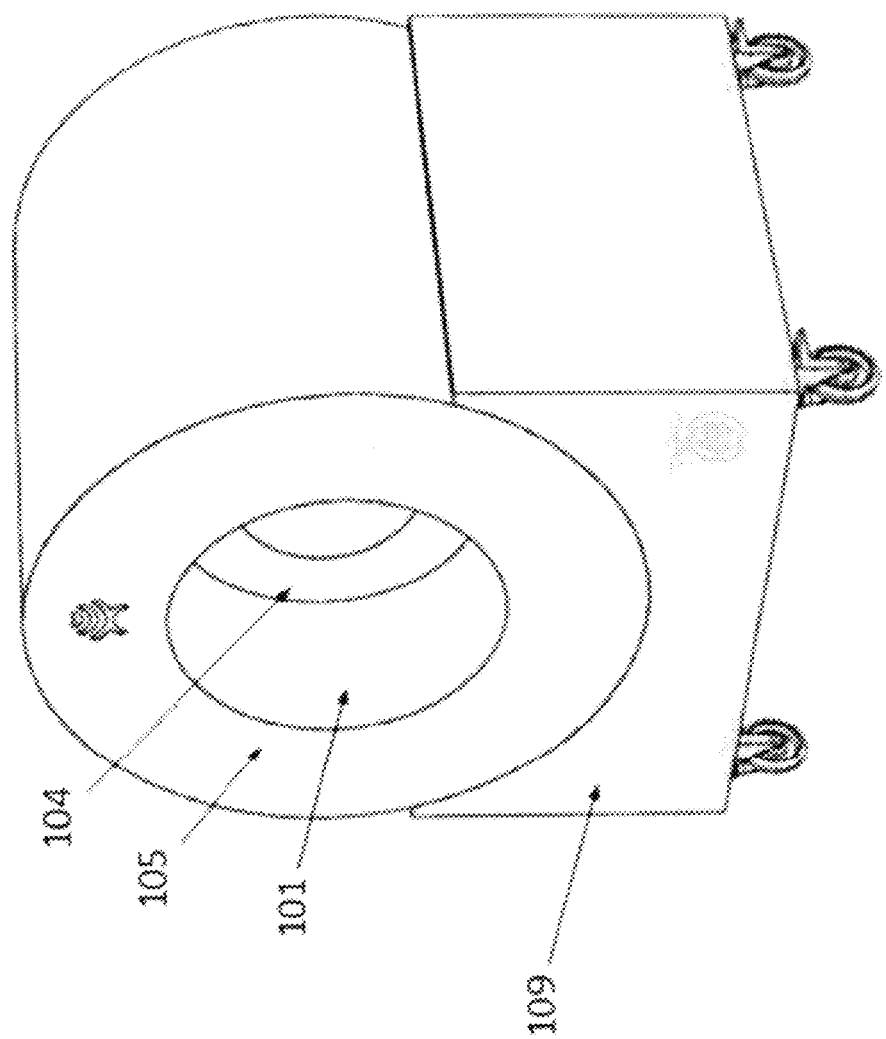
FIG. 1 shows a perspective view of an example of a magnetic resonance imaging (MRI) system configured for safe shutdown.

Referring now to FIG. 1, an example of a magnetic resonance imaging (MRI) system 100 is shown in which a magnet housing 105 is placed on a base 109. Base 109 may include a portable cart, as shown. In some installations, base 109 may be affixed to the floor of the scanning room. Magnet housing 105 includes a solenoid magnet and bore area 101, where a human patient may be placed to be scanned. The solenoid magnet may be generally known as the main magnet. The solenoid magnet may generate a substantially uniform magnetic field for imaging the human patient placed inside bore area 101. This magnetic field may generally serve as a static polarizing field.

Figure 2:
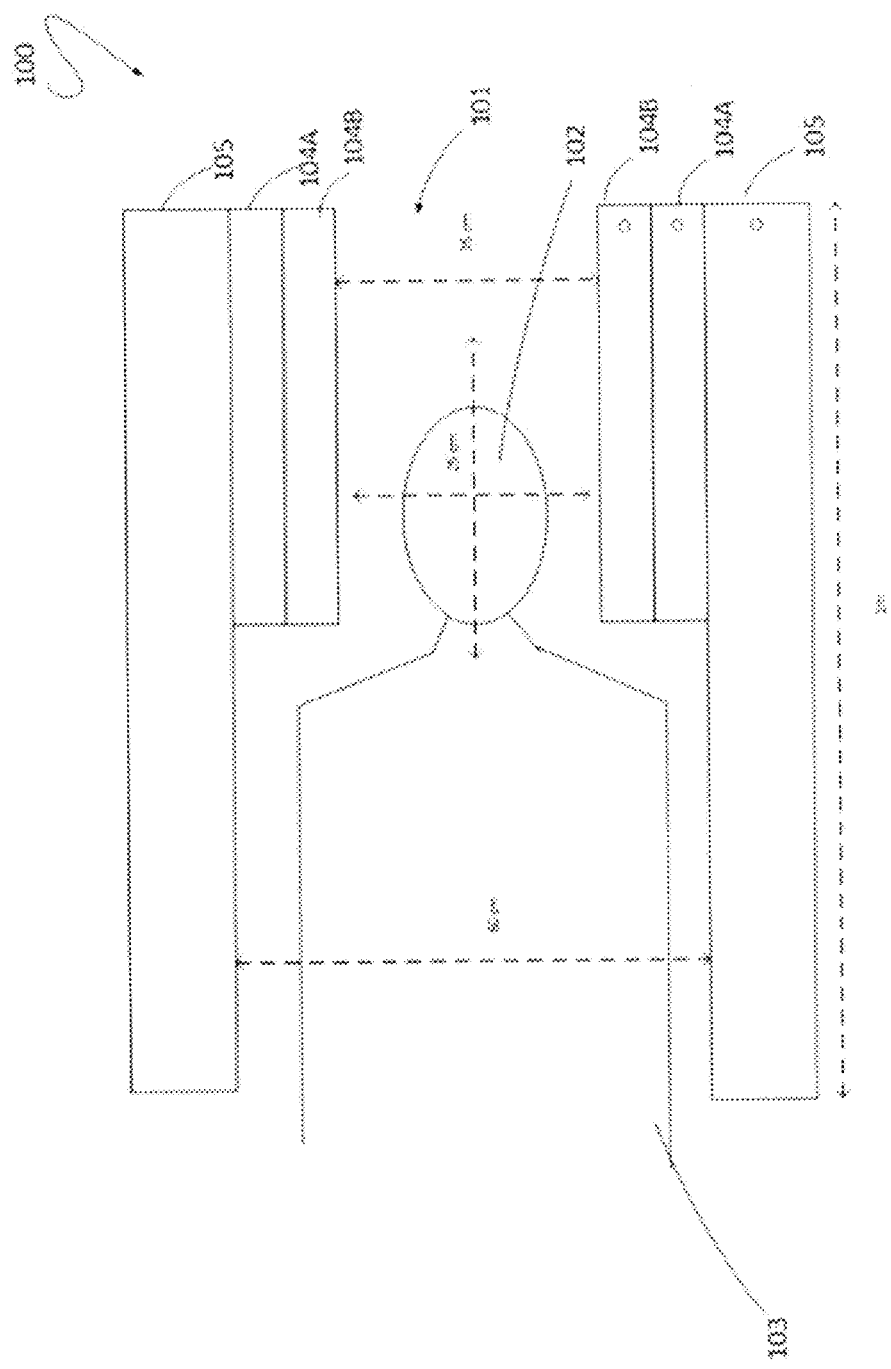
FIG. 2 shows a profile view of the MRI system configured for safe shutdown.

Referring to FIG. 1, patient 103 may be placed in bore area 101. In this example, patient head area 102 is placed inside the magnetic field to be imaged by coil assembly 104. As shown in FIGS. 1 and 2, coil assembly 104 is shaped as an annular structure and housed within the inner bore of solenoid magnet. In this example, coil assembly 104 includes a gradient coil 104A and an RF coil 104B. The gradient coil 104A may generate a perturbation of the static polarizing field to encode magnetizations within the human patient's body. In some configurations, coil assembly 104 may include a radio frequency (RF) coil 104B to transmit RF pulses as excitation pulses. The RF coil 104B may also be configured to receive MR signals from the human patient in response to the RF pulses. In some instances, housing 105 may include separate receive coils to receive the MR signals from the human patient. In these instances, radio-frequency (RF) signals are, for example, transmitted by local coils for imaging a subject. In one example, a head coil in a birdcage configuration is used for both transmitting and receiving RF signals for imaging the subject's head area 102. In another instance, a surface coil is used for transmitting an RF signal into the subject and a phased array coil configuration is used for receiving MR signals in response.

Figure 3:
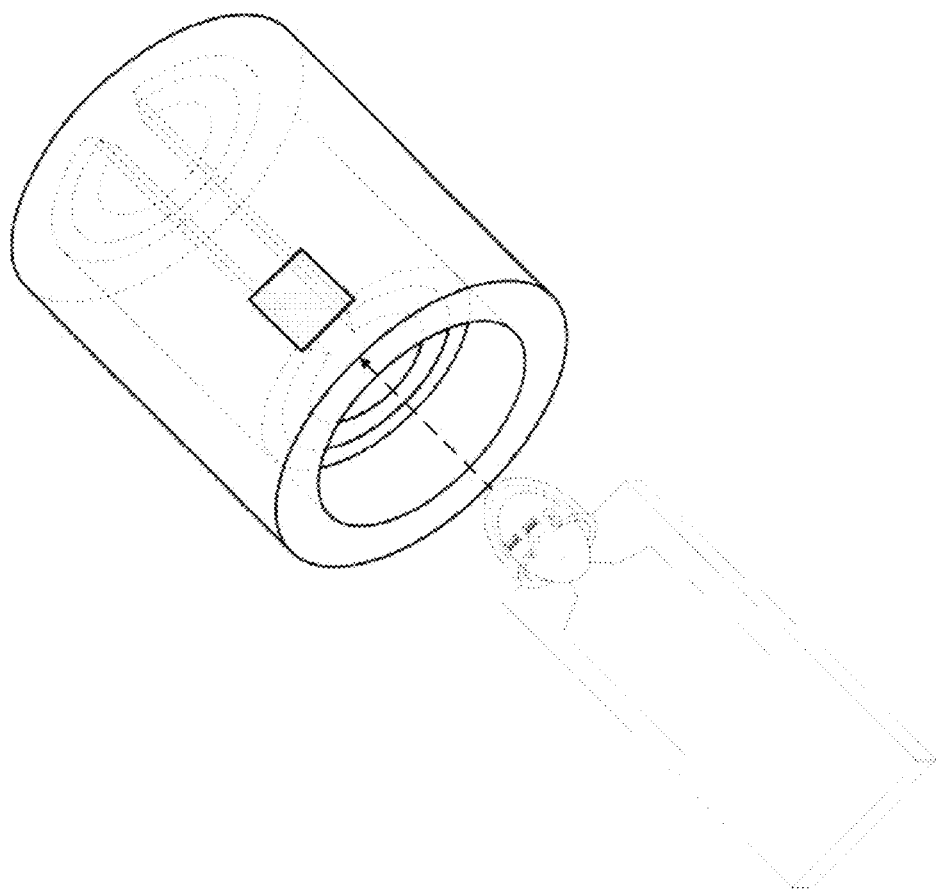
FIG. 3 shows an example embodiment illustrating the insertion of patient, wearing a head coil, into a magnetic resonance imaging system having a coil assembly with an aperture formed therein.

FIG. 3 shows an example embodiment illustrating the insertion of patient 160, supported by a table or stretcher 180, and wearing a head coil 230, into a magnetic resonance imaging system having a coil assembly with an aperture formed therein. In one instance, head coil 230 may be configured as a radio-frequency receiver cool as a local coil. In this instance, head coil 230 is configured to receive radio-frequency signals emitted from within the subject's head and in response to excitation radio, frequency pulses sent from the transmit coil 130 within the annular coil assembly 135. In another instance, head coil 230 may be configured as a radio-frequency transmit and receiver coil. In the example embodiment shown, the aperture includes a display device, screen and/or camera 252. The coil assembly and associated aperture may be rotatable to accommodate multiple patient orientations. The system includes an initial gap region 240 configured to accommodate the patient's shoulders and torso. The receiving coil may be positioned about the patient with the aperture as desired prior to installing them within the magnet. In this embodiment, the rotating coil assembly 135 includes the gradient coil 120 and transmitting coil 130.

Figure 4:
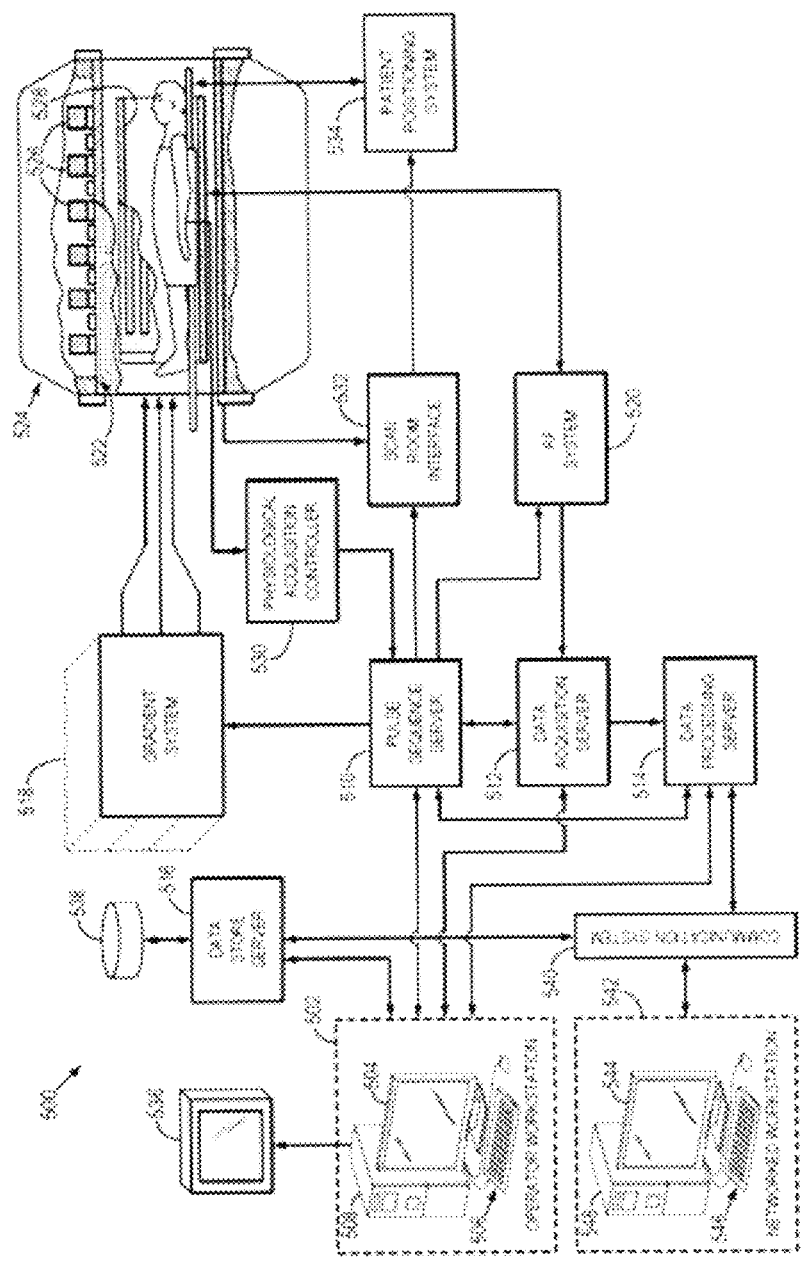
FIG. 4 is a block diagram of an example of an MRI system.

Referring particularly now to FIG. 4, an example of a magnetic resonance imaging ("MRI") system 500 is illustrated. The MRI system 500 includes an operator workstation 502, which will typically include a display 504; one or more input devices 506, such as a keyboard and mouse; and a processor 508. The processor 508 may include a commercially available programmable machine running a commercially available operating system. The operator workstation 502 provides the operator interface that enables scan prescriptions to be entered into the MRI system 500. In general, the operator workstation 502 may be coupled to four servers: a pulse sequence server 510; a data acquisition server 512; a data processing server 514; and a data store server 516. The operator workstation 502 and each server 510, 512, 514, and 516 are connected to communicate with each other. For example, the servers 510, 512, 514, and 516 may be connected via a communication system 540, which may include any suitable network connection, whether wired, wireless, or a combination of both. As an example, the communication system 540 may include both proprietary or dedicated networks, as well as open networks, such as the internet.

The pulse sequence server 510 functions in response to instructions downloaded from the operator workstation 502 to operate a gradient system 518 and a radio-frequency ("RF") system 520. Gradient waveforms necessary to perform the prescribed scan are produced and applied to the gradient system 518, which excites gradient coils in an assembly 522 to produce the magnetic field gradients $G_x$, $G_y$, and $G_z$ used for position encoding magnetic resonance signals. The gradient coil assembly 522 forms part of a magnet assembly 524 that includes a polarizing magnet 526 and a whole-body RF coil 528.

RF waveforms are applied by the RF system 520 to the RF coil 528, or a separate local coil (not shown in FIG. 4), in order to perform the prescribed magnetic resonance pulse sequence. Responsive magnetic resonance signals detected by the RF system 528, or a separate local coil (not shown in FIG. 4), are received by the RF system 520, where they are amplified, demodulated, filtered, and digitized under direction of commands produced by the pulse sequence server 510. The RF system 520 includes an RF transmitter for producing a wide variety of RF pulses used in MRI pulse sequences. The RF transmitter is responsive to the scan prescription and direction from the pulse sequence server 510 to produce RF pulses of the desired frequency, phase, and pulse amplitude waveform. The generated RF pulses may be applied to the whole-body RF coil 528 or to one or more local coils or coil arrays (not shown in FIG. 4).

The RF system 520 also includes one or more RF receiver channels. Each RF receiver channel includes an RF preamplifier that amplifies the magnetic resonance signal received by the coil 528 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (1)$$

and the phase of the received magnetic resonance signal may also be determined according to the following relationship:

$$\varphi = \tan^{-1}\left(\frac{Q}{I}\right). \qquad (2)$$

The pulse sequence server 510 also optionally receives patient data from a physiological acquisition controller 530. By way of example, the physiological acquisition controller 530 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 510 to synchronize, or "gate," the performance of the scan with the subject's heart beat or respiration.

The pulse sequence server 510 also connects to a scan room interface circuit 532 that receives signals from various sensors associated with the condition of the patient and the magnet system. It is also through the scan room interface circuit 532 that a patient positioning system 534 receives commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, such that no data is lost by data overrun. In some scans, the data acquisition server 512 does little more than pass the acquired magnetic resonance data to the data processor server 514. However, in scans that require information derived from acquired magnetic resonance data to control the further performance of the scan, the data acquisition server 512 is programmed to produce such information and convey it to the pulse sequence server 510. For example, during prescans, magnetic resonance data is acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also be employed to process magnetic resonance signals used to detect the arrival of a contrast agent in a magnetic resonance angiography ("MRA") scan. By way of example, the data acquisition server 512 acquires magnetic resonance data and processes it in real-time to produce information that is used to control the scan.

The data processing server 514 receives magnetic resonance data front the data acquisition server 512 and processes it in accordance with instructions downloaded from the operator workstation 502. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 514 are conveyed back to the operator workstation 502 where they are stored. Real-time images are stored in a data base memory cache (not shown in FIG. 4), from which they may be output to operator display 504 or a display 536 that is located near the magnet assembly 524 for use by attending physicians. Batch mode images or selected real time images are stored in a host database on disc storage 538. When such images have been reconstructed and transferred to storage, the data processing server 514 notifies the data store server 516 on the operator workstation 502. The operator workstation 502 may be used by an operator to archive the images, produce films, or send the images via a network to other facilities.

The MRI system 500 may also include one or more networked workstations 542. By way of example, a networked workstation 542 may include a display 544; one or more input devices 546, such as a keyboard and mouse; and a processor 548. The networked workstation 542 may be located within the same facility as the operator workstation 502, or in a different facility, such as a different healthcare institution or clinic.

The networked workstation 542, whether within the same facility or in a different facility as the operator workstation 502, may gain remote access to the data processing server 514 or data store server 516 via the communication system 540. Accordingly, multiple networked workstations 542 may have access to the data processing server 514 and the data store server 516. In this manner, magnetic resonance data, reconstructed images, or other data may be exchanged between the data processing server 514 or the data store server 516 and the networked workstations 542, such that the data or images may be remotely processed by a networked workstation 542. This data may be exchanged in any suitable format, such as in accordance with the transmission control protocol ("TCP"), the internet protocol ("IP"), or other known or suitable protocols.

Figure 5:
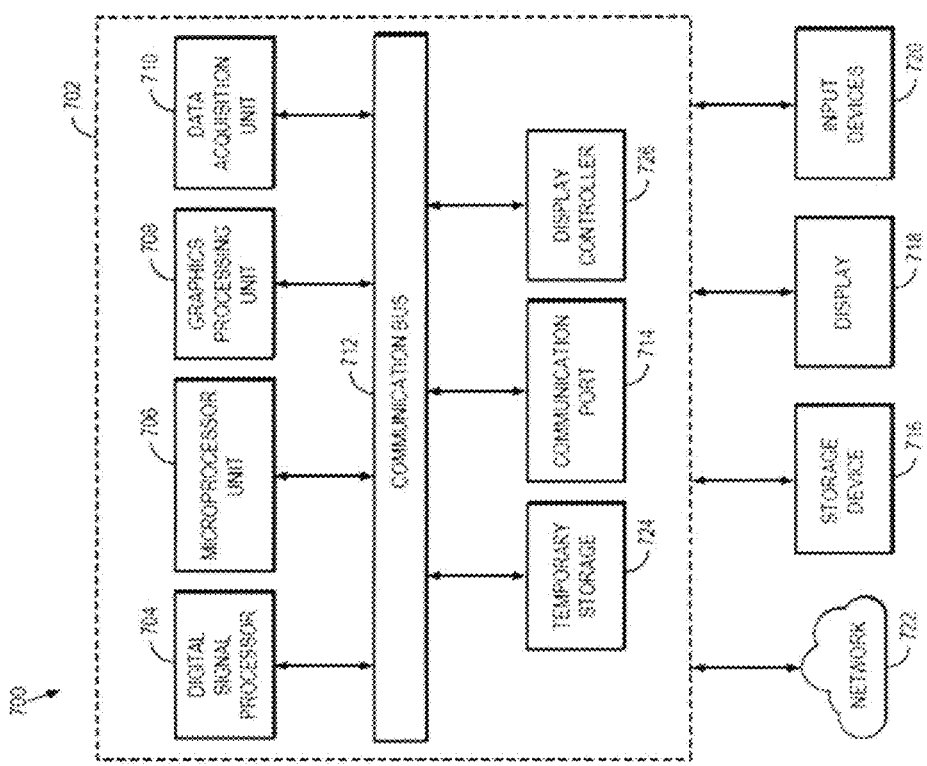
FIG. 5 is a block diagram of an example computer system that may be configured to implement the methods described herein.

Referring now to FIG. 5, a block diagram of an example computer system 700 that may be configured to co-register medical images acquired with different imaging modalities, as described above, is illustrated. The medical images to be co-registered may be provided to the computer system 700 from the respective medical imaging systems, such as an MRI system and a CT system, or from a data storage device, and are received in a processing unit 702.

In some embodiments, the processing unit 702 may include one or more processors. As an example, the processing unit 702 may include one or more of a digital signal processor ("DSP") 704, a microprocessor unit ("MPU") 706, and a graphics processing unit ("GPU") 708. The processing unit 702 may also include a data acquisition unit 710 that is configured to electronically receive data to be processed, which may include first and second medical images, image series, or image volumes. The DSP 704, MPU 706, GPU 708, and data acquisition unit 710 are all coupled to a communication bus 712. As an example, the communication bus 712 may be a group of wires, or a hardwire used for switching data between the peripherals or between any component in the processing unit 702.

The DSP 704 may be configured to receive and processes the first and second medical images. The MPU 706 and GPU 708 may also be configured to process the first and second medical images in conjunction with the DSP 704. As an example, the MPU 706 may be configured to control the operation of components in the processing unit 702 and may include instructions to perform processing of the first and second medical images on the DSP 704. Also as an example, the GPU 708 may process image graphics.

In some embodiments, the DSP 704 may be configured to process the first and second medical images received by the processing unit 702 in accordance with the algorithms described above. Thus, the DSP 704 may be configured to identify anatomical features in the images, to calculate registration parameters based on the identified anatomical features and known spatial relationships there between, and to co-register the images using the registration parameters.

The processing unit 702 preferably includes a communication port 714 in electronic communication with other devices, which may include a storage device 716, a display 718, and one or more input devices 720. Examples of an input device 720 include, but are not limited to, a keyboard, a mouse, and a touch screen through, which a user may provide an input.

The storage device 716 is configured to store images, whether provided to or processed by the processing unit 702. The display 718 is used to display images, such as images that may be stored in the storage device 716, and other information. Thus, in some embodiments, the storage device 716 and the display 718 may be used for displaying the images before and after registration and for outputting other information, such as data plots or other reports based on the registration process.

The processing unit 702 may also be in electronic communication with a network 722 to transmit and receive data, including CT images, MR images, and other information. The communication port 714 may also be coupled to the processing unit 702 through a switched central resource, for example the communication bus 712.

The processing unit 702 may also include a temporary storage 724 and a display controller 726. As an example, the temporary storage 724 may store temporary information. For instance, the temporary storage 724 may be a random access memory.

Implementations relating to scan queue management are next described which may be used within MRI devices and/or systems described heretofore, and/or within other medical imaging systems and/or devices.

Figure 6:
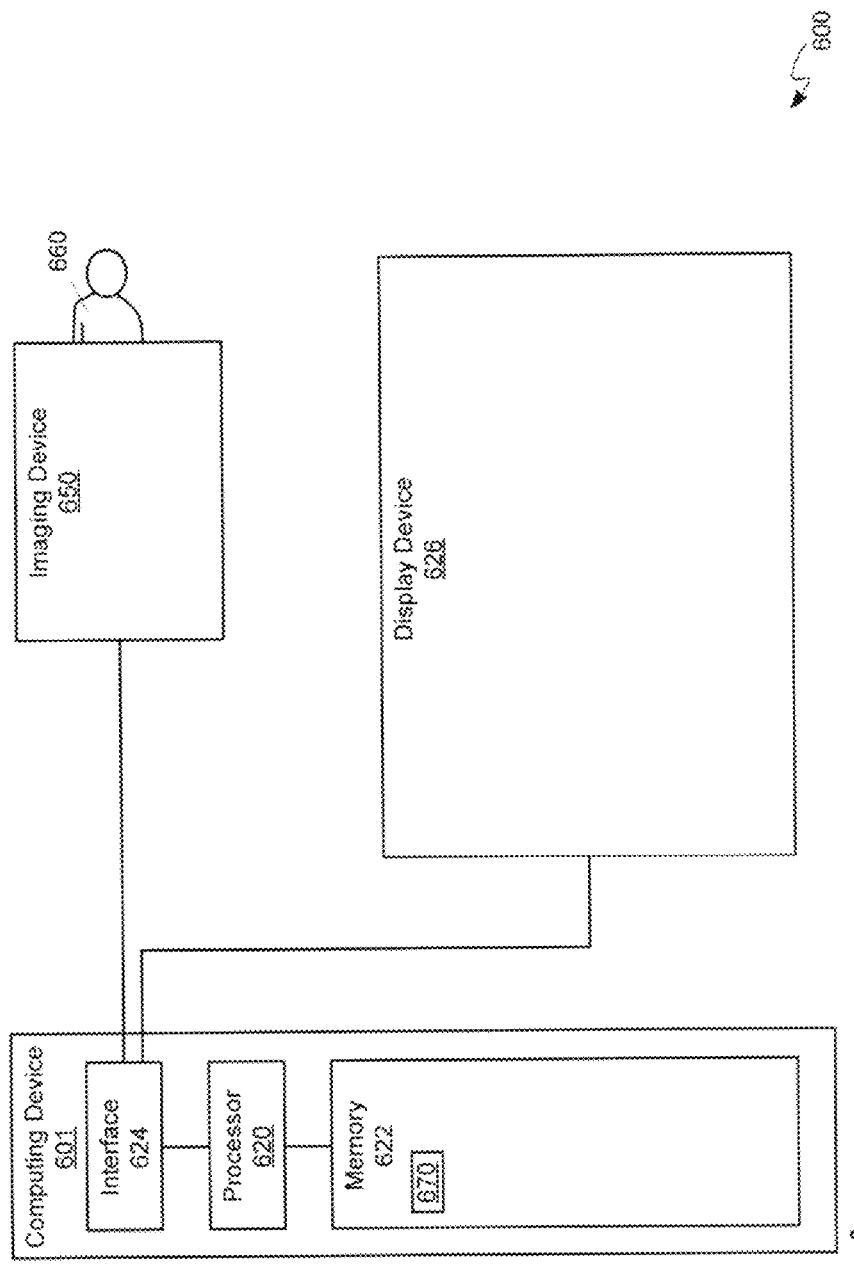
FIG. 6 depicts a medical imaging system for scan queue management, according to non-limiting implementations.

Hence, attention is next directed to FIG. 6, which depicts a medical Imaging system 600 for scan queue management, medical imaging system 600 comprising: a computing device 601 comprising a processor 620, a memory 622, and a communication interface 624; a display device 626; and an imaging device 650 configured to acquire digital images, computing device 601 configured to communicate with display device 626 and imaging device 650 using communication interface 624, communication with imaging device 650 occurring for a duration of a scan queue series, processor 620 configured to: generate a scan prescription comprising instructions for causing imaging device 650 to acquire a plurality of digital image series, each of the plurality of digital image series comprising a respective series of digital images; render, at display device 626: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series; transmit, using communication interface 624, the scan prescription to imaging device 650; render, at display device 626, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated; receive, from imaging device 650, using communication interface 624, the respective digital image series as the respective digital image series are acquired; store, at memory 622, the respective digital image series; and when acquisition of the respective digital image series has occurred, render, at display device 626, a graphical indicator of a next respective digital image series to be acquired in the graphical scan queue. For example, some MRI sequences may be cardiac or respiratory gated; hence a scan time may be affected by heart rate and/or breathing rate and a progress indicator indicating remaining lines of data to be acquired may be provided, for example as an acquisition progress indicator.

Computing device 601 may comprise one or more of operator workstation 502, networked workstation 542, depleted in FIG. 4, and computer system 700, depicted in FIG. 5, with processor 620, memory 622 and communication interface 624 corresponding to suitable components of operator workstation 502, networked workstation 542, and/or computer system 700; hence, while not depicted, computing device 601 may also comprise other components such as one or more input devices. Display device 626 may comprise a display device of one or more of operator workstation 502, networked workstation 542, and/or computer system 700, and may be integrated with computing device 601 and/or comprise a stand-alone display device, such as a monitor and the like, in particular, display device 626 may comprise any suitable one of or combination of CRT (cathode ray tube) and/or flat panel displays (e.g. LCD (liquid crystal display), plasma, OLED (organic light emitting diode), capacitive or resistive touch screens, and the like. In some implementations, display device 626 comprises a touch screen, such that display device 626 comprise an input device.

While MRI devices have been described in detail heretofore, other types of imaging devices that use scan prescriptions as described herein are within the scope of present implementations. As such, imaging device 650 may comprise one or more of: a magnetic resonance imaging (MRI) device, an Optical Coherence Tomography (OCT) device, a computerized tomography (CT) device a computerized axial tomography (CAT) device, and a positron emission tomography (PET) device. Regardless, imaging device 650 is generally configured to acquire digital images of a sample, which may include, but is no limited to, a patient 660, as depicted.

Processor 620 may be implemented as a plurality of processors, including but not limited to one or more central processors (CPUs) and/or one or more processing units; either way, processor 620 comprises a hardware element and/or a hardware processor of computing device 601. Processor 620 is configured to communicate with memory 622 comprising a non-volatile storage unit (e.g. Erasable Electronic Programmable Read Only Memory ("EEPROM"), Flash Memory) and a volatile storage unit (e.g. random access memory ("RAM")). Furthermore, when processor 620 is implemented as a plurality of processors, at least a first processor may be configured to communicate with imaging device 650 using interface 624, and at least a second processor may be configured to communicate with display device 626; the various processors may be in communication with each other. Programming instructions that implement the functional teachings of computing device 601 as described herein are typically maintained, persistently, in memory 622 and used by processor 620 which makes appropriate utilization of volatile storage during the execution of such programming instructions. Those skilled in the art recognize that memory 622 is an example of computer readable media that may store programming instructions executable on processor 620. Furthermore, memory 622 is also an example of a memory unit and/or memory module and/or a non-volatile memory.

In particular, memory 622 stores an application 670 comprising a computer program, wherein execution of the computer program, for example by processor 620, is for: generating a scan prescription comprising instructions for causing imaging device 650 to acquire a plurality of digital image series, each of the plurality of digital image series comprising a respective series of digital images; rendering, at display device 626: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series; transmitting, using communication interface 624, the scan prescription to imaging device 650; rendering, at display device 626, a respective graphical timer on each respective first graphical representation as each of the respective digital image series are acquired, the respective graphical timer indicating one or more of a time remaining to acquire the respective digital image series and acquisition progress, the graphical indication of the total estimated time undated as the respective graphical timer is updated; receiving, from imaging device 650, using communication interface 624, the respective digital image series as the respective digital image series are acquired; storing, at memory 622, the respective digital image series: and, when acquisition of the respective digital image series has occurred, rendering, at display device 626, a graphical indicator of a next respective digital image series to be acquired in the graphical scan queue.

Figure 7:
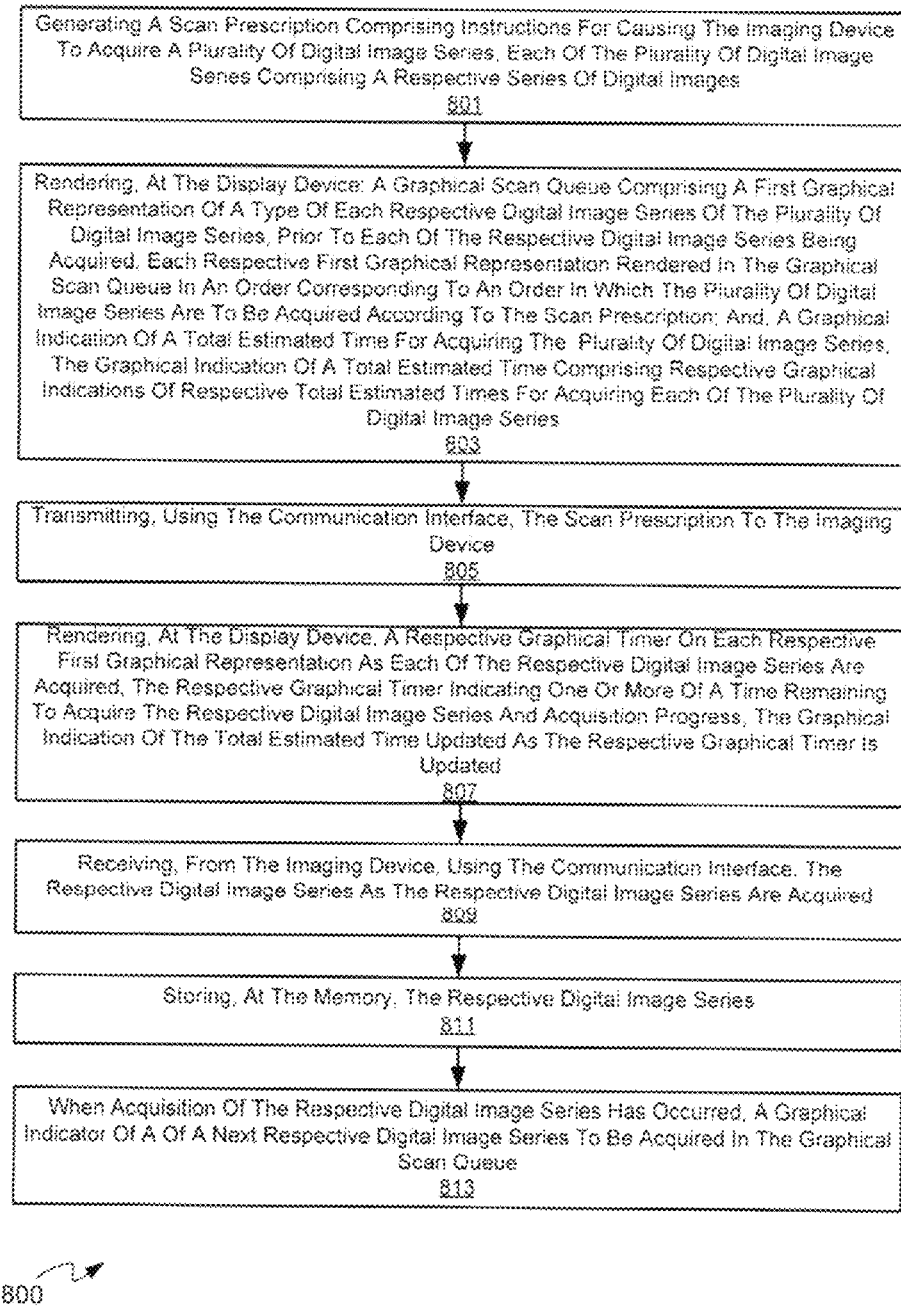
FIG. 7 depicts a method for scan queue management in a medical imaging system, according to non-limiting implementations.

Attention is now directed to FIG. 7 which depicts a flow-chart of a method 800 for scan queue management in a medical imaging system, according to non-limiting implementations. In order to assist in the explanation of method 800, it will be assumed that method 800 is performed using system 600, and specifically by processor 620 of computing device 601, for example when processor 620 processes application 670. Indeed, method 800 is one way in which computing device 101 may be configured. Furthermore, the following discussion of method 800 will lead to a further understanding of computing device 601, and system 600 and its various components. However, it is to be understood that system 600 and/or method 800 may be varied, and need not work exactly as discussed herein in conjunction with each other, and that such variations are within the scope of present implementations.

Regardless, it is to be emphasized, that method 800 need not be performed in the exact sequence as shown, unless otherwise indicated; and likewise various blocks may be performed in parallel rather than in sequence; hence the elements of method 800 are referred to herein as "blocks" rather than "steps". It is also to be understood, however, that method 800 may be implemented on variations of system 600 as well.

At block 801, processor 620 generates a scan prescription comprising instructions for causing imaging device 650 to acquire a plurality of digital image series, each of the plurality of digital image series comprising a respective series of digital images.

At block 803, processor 620 renders, at display device 626: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series. Block 803 may include reconstructing digital images from data acquired from imaging device 650.

At block 805, processor 620 transmits, using communication interface 624, the scan prescription to imaging device 650

At block 807, processor 620 renders, at display device 626, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated.

At block 809, processor 620 receives, from imaging device 650, using communication interface 624, the respective digital image series as the respective digital image series are acquired.

At block 811, processor 620 stores, at memory 622, the respective digital image series.

At block 813, processor 620, when acquisition of the respective digital image series has occurred, renders at display device 626, a graphical indicator of a next respective digital image series to be acquired in the graphical scan queue.

Method 800 will now be discussed with reference to FIGS. 8 to 19. For example, attention is next directed to FIG. 8, which depicts display device 626 rendering a graphic user interface (GUI) 900 under control of processor 620, for example when processor 620 is processing application 670, and processor 620 is implementing method 800. It is assumed in FIG. 8 that display device 626 comprises a touchscreen such that touch input may be received at display device 626 to control operation of computing device 601 and/or imaging device 650.

GUI 900 comprises: selectable options 901, 902, 903 which, when selected, causes processor 620 to control one or more of computing device 601 and imaging device 650 to operate in one or more modes, the one or more modes including one or more of: a setup mode wherein a scan prescription is generated; a scan mode wherein a plurality of digital image series is acquired; and a view mode wherein the plurality of digital image series are rendered at display device 626.

Figure 8:
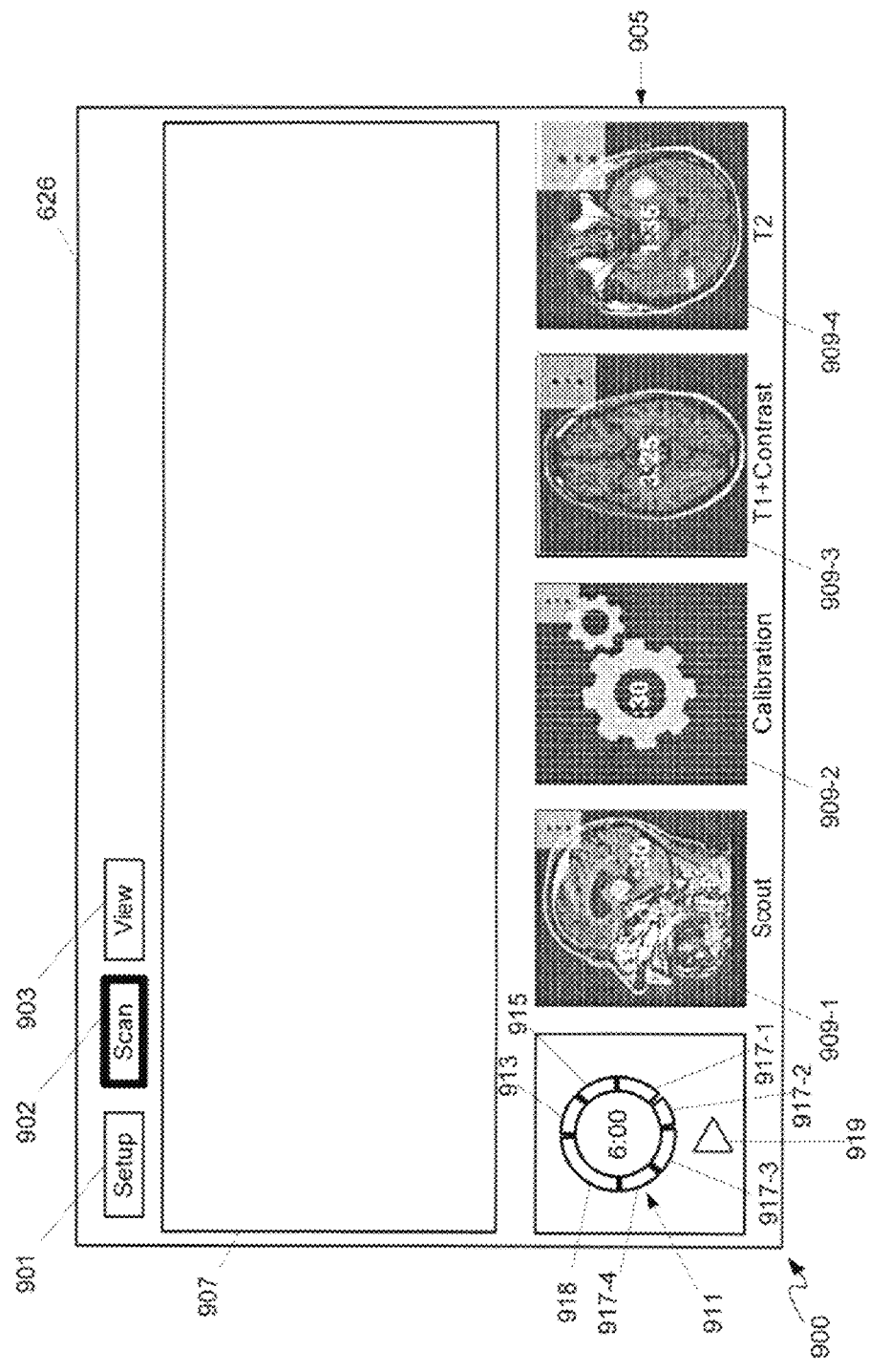
FIG. 8 depicts a first sequence of scan queue management being at least partially implemented using a display device of the system of FIG. 6, according to non-limiting implementations.

For example, selectable option 901, when selected, causes processor 620 to control at least computing device 601 to enter a setup mode (hence the label "Setup" on selectable option 901), wherein a scan prescription is generated. Similarly, selectable option 902, when selected, causes processor 620 to control at least computing device 601 and imaging device 650 to enter a scan mode (hence the label "Scan" on selectable option 901), wherein a plurality of digital image series is acquired. And, selectable option 903, when selected, causes processor 620 to control at least computing device 601 to enter a view mode (hence the label "View" on selectable option 901), wherein the plurality of digital image series are rendered at display device 626. Hence, each of selectable options 901, 902, 903 may comprise virtual buttons and the like, however other processes and/or methods for mode selection are within the scope of present implementations, including, but not limited to selecting a mode using pulldown menus and the like. Hence, selectable options 901, 902, 903, as depicted in FIG. 8, may be optional.

As depicted, selectable option 902 is selected as indicated by lines selectable option 902 being of a heavier weight than respective lines of selectable option 901, 903.

GUI 900 further comprises a graphical scan queue 905 described in further detail below. GUI 900 further comprises an information area 907 adjacent graphical scan queue 905. Hence, processor 620 may be configured to render, at display device 626, information area 907 adjacent graphical scan queue 905; and render contextual operational information in information area 907 according to a mode in which the medical imaging system 600 is currently operating. For example, contextual information may be rendered in information area 907 according to a mode selected using selectable options 901, 902, 903.

For example, while not depicted, when selectable option 901 is selected, processor 620 may render, in information area 907, options and/or data and/or input fields for generating a scan prescription. Such options and/or data and/or input fields may include but are not limited to, selecting types of scans that are to occur at imaging device 650, selecting an order of such scans, and selecting parameters associated with each type of scan that are to occur at imaging device 650. For example, when imaging device 650 comprises an MRI device, types of scans that may occur include, but are not limited to, scout scans, calibration scans, T1 scans, T1+contrast scans, T2 scans and the like. Similarly, when selectable option 903 is selected, processor 620 may render, in information area 907 digital images acquired from imaging device 650 with options for viewing and/or editing such digital images.

In any event, in the setup mode, processor 620 generates a scan prescription comprising instructions for causing imaging device 650 to acquire a plurality of digital image series, each of the plurality of digital image series comprising a respective series of digital images, for example each of the plurality of digital image series comprising respective series of digital images acquired in a respective scan mode (e.g. block 801 of method 800).

However, scan prescriptions may also be generated by processor 620 using other processes and/or methods. For example, processor 620 may receive data configured to generate a scan prescription from another computing device via interface 624 and/or processor 620 may receive data configured to generate a scan prescription using other selectable options, including, but not limited to, pulldown menus and the like. In other words, such data may be received using inputs other than optional information area 907.

It is assumed in FIG. 8 that scan prescription has been generated and that the scan prescription includes instructions for causing imaging device 650 to acquire a plurality of digital image series using at least a scout scan, a calibration scan, a T1+contrast scan an a T2 scan, assuming that imaging device 650 comprises an MRI device. It is further assumed in FIG. 8 that system 600 is in a scan mode as selectable option 902 is selected.

Hence, processor 620 is further configured to render, at display device 626; graphical scan queue 905 comprising a first graphical representation 909-1, 909-2, 909-3, 909-4 of a type of each respective digital image series of the plurality of digital image series, prior to each of she respective digital image series being acquired, each respective first graphical representation 909-1, 909-2, 909-3, 909-4 rendered in the graphical scan queue 905 in an order corresponding to an order in which the plurality of digital image series are to be acquired according to the scan prescription. First graphical representation 909-1, 909-2, 903-3, 909-4 will be interchangeably referred to hereafter, collectively, as first graphical representations 909 and generically as a first graphical representation 909.

In other words, each of first graphical representations 909 correspond to a scan type in the scan prescription, and the first graphical representations 909 are rendered in an order in graphical scan queue 905 in which respective scan are to occur according to the scan prescription.

For example, as depicted, processor 620 renders each respective first graphical representation 909 rendered in graphical scan queue 905 in the order by rendering each respective first graphical representation 909 rendered in graphical scan queue 905 side-by-side with each other. As depicted first graphical representations 909 are rendered in a row; however, in other implementations, first graphical representations 909 may be rendered in one or more of a column, a diagonal, in a line, and the like.

In some implementations, as depicted, each first graphical representation 909 comprises a textual indication of a type of scan associated with an operational mode of imaging device 650 when acquiring the respective digital image series; for example, each first graphical representation 909 respectively comprise, in order text "Scout", "Calibration", "T1+contrast", and "T2".

However, types of scans may also be indicated graphically; indeed, as depicted, each image rendered in each first graphical representation 909 comprises an image associated with a type of scan that is to occur in association with each first graphical representation 909. For example, each of the depicted images in each first graphical representation 909 may be selected from images acquired in previous scans of the same type and/or from graphics associated with the scan type. For example, depicted respective images in first graphical representations 909-1, 909-2, 909-4 each comprise images acquired in previous scans of the same type, while a depicted image in first graphical representations 909-2 comprise a graphic associated with a "Calibration" scan type.

As depicted, each of first graphical representations 909 comprises a respective estimated amount of time for acquiring a respective digital image series. For example, first graphical representation 909 comprises a time ":30" indicating that an estimated amount of time to perform the associated "Scout" scan is about 30 seconds; similarly, first graphical representations 909-2, 909-3, 909-4 comprises respective times ":30", "3:25", "1:35" indicating that an estimated amount of time to perform the associated "Calibration" scan, "T1+Contrast" scan and "T2" scan is respectively about 30 seconds, about 3 minutes and 25 seconds, and about 1 minute and 35 seconds.

Hence, as depicted, processor 620 is further configured to, render, at display device 626, estimated times to acquire respective graphical image series on each of respective first graphical representations 909 prior to each of the respective digital image series being acquired.

As further depicted in FIG. 8, processor 620 is further configured to render a graphical indication 911 of a total estimated time for acquiring the plurality of digital image series. For example, the total estimated time for acquiring the plurality of digital image series from each of the scan associated with each of the first graphical representations 909 is about 6 minutes, which is indicated in graphical indication 911. However, graphical indication 911 of the total estimated time further comprises respective graphical indications of respective total estimated times for acquiring each of the plurality of digital image series.

For example, as depicted, graphical indication 911 of the total estimated time comprises a segmented annulus, wherein at least one segment in the segmented annulus corresponds to a time to perform individual scans associated with first graphical representations 909. For example, a first segment 913 of the segmented annulus corresponds to the about 30 seconds of the "Scout" scan associated with first graphical representation 909-1; similarly, a next and/or second segment 915 (going clockwise around the segmented annulus), corresponds to the about 30 seconds of the "Calibration" scan associated with first graphical representation 909-2; next and/or third segments 917-1, 917-2, 917-3, 917-4 (going clockwise around the segmented annulus), corresponds to the about 3 minutes 25 seconds of the "T1+Contrast" scan associated with first graphical representation 909-3; and next and/or fourth segment 918 (going clockwise around the segmented annulus), corresponds to the about 1 minutes 35 seconds of the "T2" scan associated with first graphical representation 909-4. Four segments 917-1, 917-2, 917-3, 917-4 are associated with first graphical representation 909-3 as three sets of digital images are acquired and one pause is injected into the scan to allow for injection of a contrast agent as described in more detail below.

In any event, rendering of graphical scan queue 905 and graphical indication 911 may correspond to block 803 of method 800.

However, other implementations of graphical indication 911 are within the scope of present implementations as long as graphical indication 911 comprises respective graphical indications of respective total estimated times for acquiring each of the plurality of digital image series. For example, other shapes, such as lines, triangles, squares, hexagons, octagons, and the like may be used to render graphical indication 911 of the total estimated time.

Furthermore, as will be described below, as each scan associated each first graphical representation 909, processor 620 will update the rendering of graphical indication 911 to show a time that has past and/or a time remaining in the total estimated time.

As depicted, processor 620 may further render a graphical control 919 adjacent graphical indication 911 of the total estimated time; when selected and/or activated (e.g. at the touchscreen of display device 626), graphical control 919 will cause the scan associated with first graphical representation 909 to begin. As depicted, graphical control 919 comprises a graphical "play" button.

Figure 9:
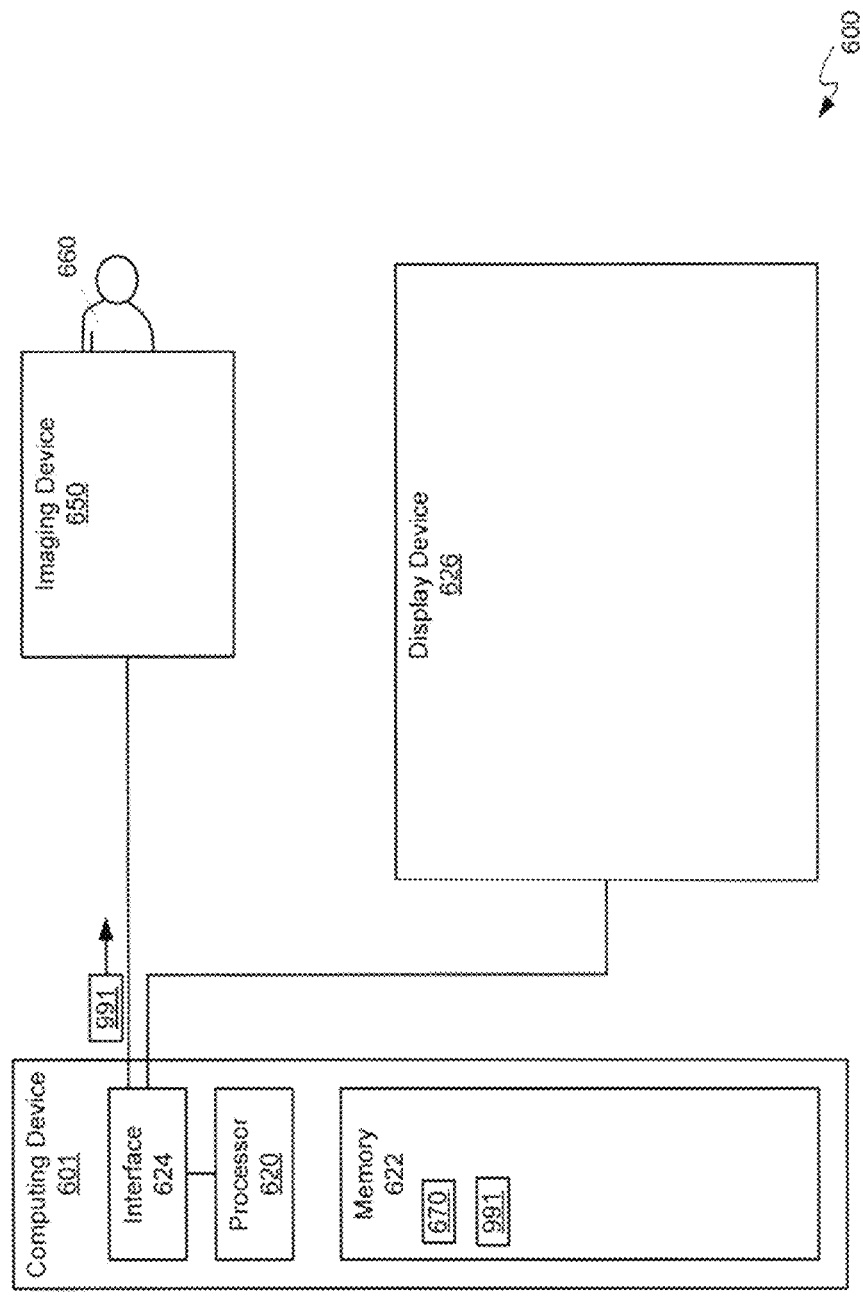
FIG. 9 depicts the system of FIG. 6 when a scan prescription is communicated to an imaging device, according to non-limiting implementations.

For example, attention is next directed to FIG. 9, which is substantially similar to FIG. 6, with like elements having like numbers. In FIG. 9, it is assumed that a scan prescription 991 has been generated, as described above, and stored in memory 622. Further, in FIG. 9, processor 620 transmits scan prescription 991 to imaging device 650 using interface 624 (e.g. block 805 of method 800). For example, such transmitting may occur when graphical control 919 is selected and/or activated at the touchscreen of display device 626, and the like. Alternatively, such transmitting may occur when scan prescription is generated and selection and/or activation of graphical control 919 causes processor 620 to transmit a command to imaging device 650 to begin the scan. Alternatively, such scanning may begin automatically when scan prescription 991 is received at imaging device 650.

It is further appreciated that communication between computing device 601 and imaging device 650 may occur for a duration of a scan queue series; for example, while scans are occurring at imaging device 650, computing device 601 and imaging device 650 may exchange data for starting and/or stopping scanning, updates on scanning, progress on scanning, time left in scanning, when scanning is paused, and the like. When scanning ends, and/or when scan queue series ends, communication between computing device 601 and imaging device 650 may end and/or be suspended until a next scan queue series occurs.

Figure 10:
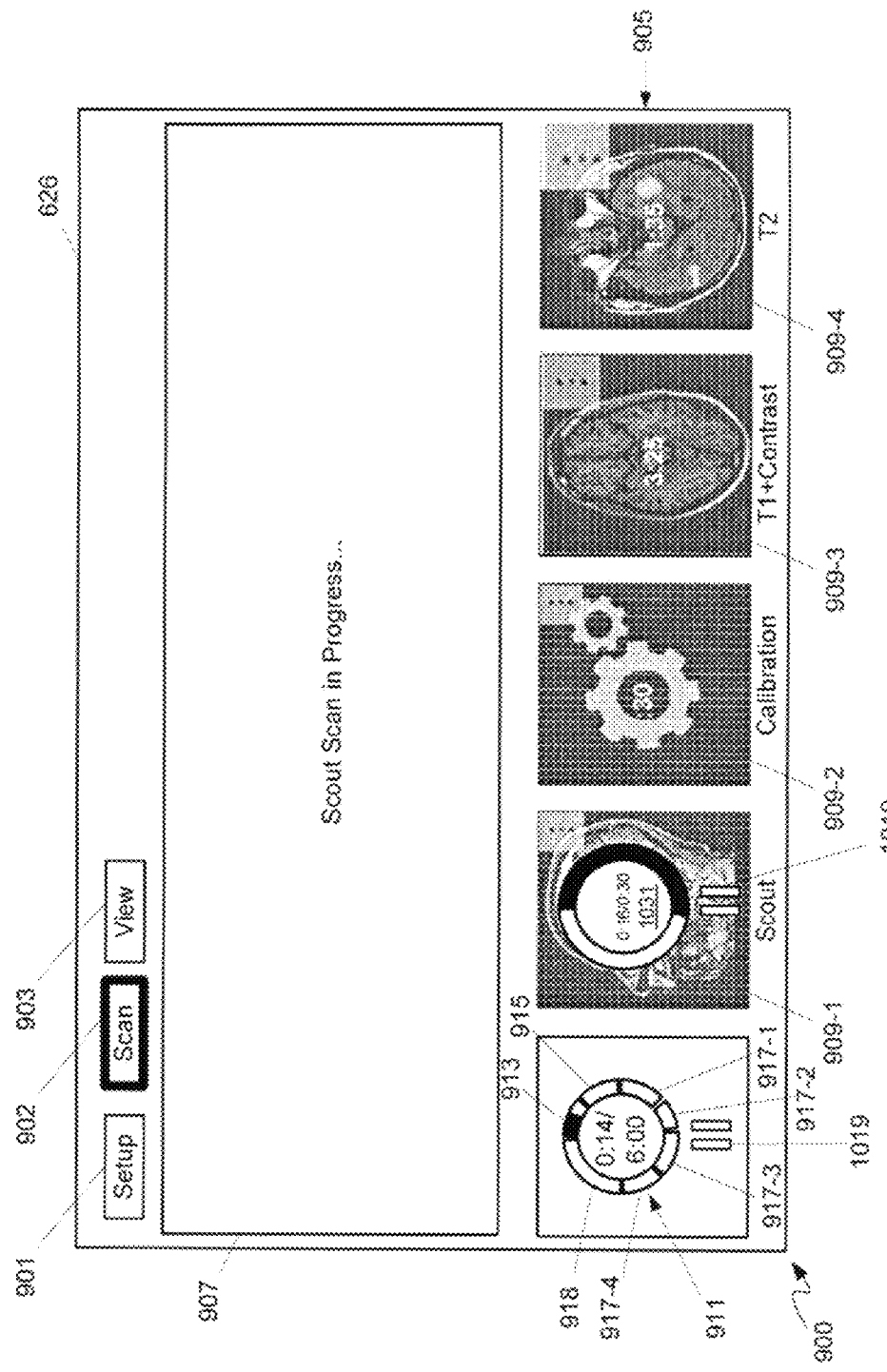
FIG. 10 depicts a second sequence of scan queue management being at least partially implemented using a display device of the system of FIG. 6, according to non-limiting implementations.

Attention is next directed to FIG. 10, which is substantially similar to FIG. 8, with like elements having like numbers. In general, FIG. 10 sequentially and/or temporally follows FIG. 8, as in FIG. 10 it is assumed that the scan associated with first representation 909-1 has started and is occurring at imaging device 650.

As such, graphical control 919 is replaced with another graphical control 1019 comprising a graphical pause button; graphical control 1019 is also rendered on first representation 909-1. When either of graphical controls 1019 are selected and/or activated, processor 620 may pause and/or stop the scan which is currently occurring at imaging device 650.

In particular, in FIG. 10, processor 620 renders, at display device 626, a respective graphical timer 1031 on each respective first graphical representation 909 as each of the respective digital image series are acquired, respective graphical timer 1031 indicating a time remaining to acquire the respective digital image series, graphical indication 911 of the total estimated time updated as the respective graphical timer 1031 is updated (e.g. block 807 of method 800).

For example, as the scan associated with first graphical representation 909-1 starts, graphical timer 1031 is rendered on first graphical representation 909-1, graphical timer 1031, as depicted, comprises a remaining amount of time left in an associated scan (e.g. 16 seconds of 30 seconds total), and furthermore, graphical timer 1031, as depicted, comprises an annulus, which changes colour based on amount of time remaining in the associated scan. For example, the black portion of the annulus indicates the time that has passed in the scan, while the white portion indicates time remaining in the scan. A respective area and/or length of each of the white portion and the black portion are proportional to a remaining time and a passed time in the scan.

Furthermore, in FIG. 10, segment 913 of graphical indication 911, which corresponds to the scan associated with first graphical representation 909-1, is updated to show progression of time in the scan; as depicted, the time that has passed is depicted as a fraction of the total time for all the scans associated with first graphical representations 909 to occur.

Furthermore, in FIG. 10, processor 620 renders, at display device 626, in information area 907, an indication that a scan associated with first graphical representation 909-1 is occurring; specifically, the text "Scout Scan in Progress . . . " is rendered.

Figure 11:
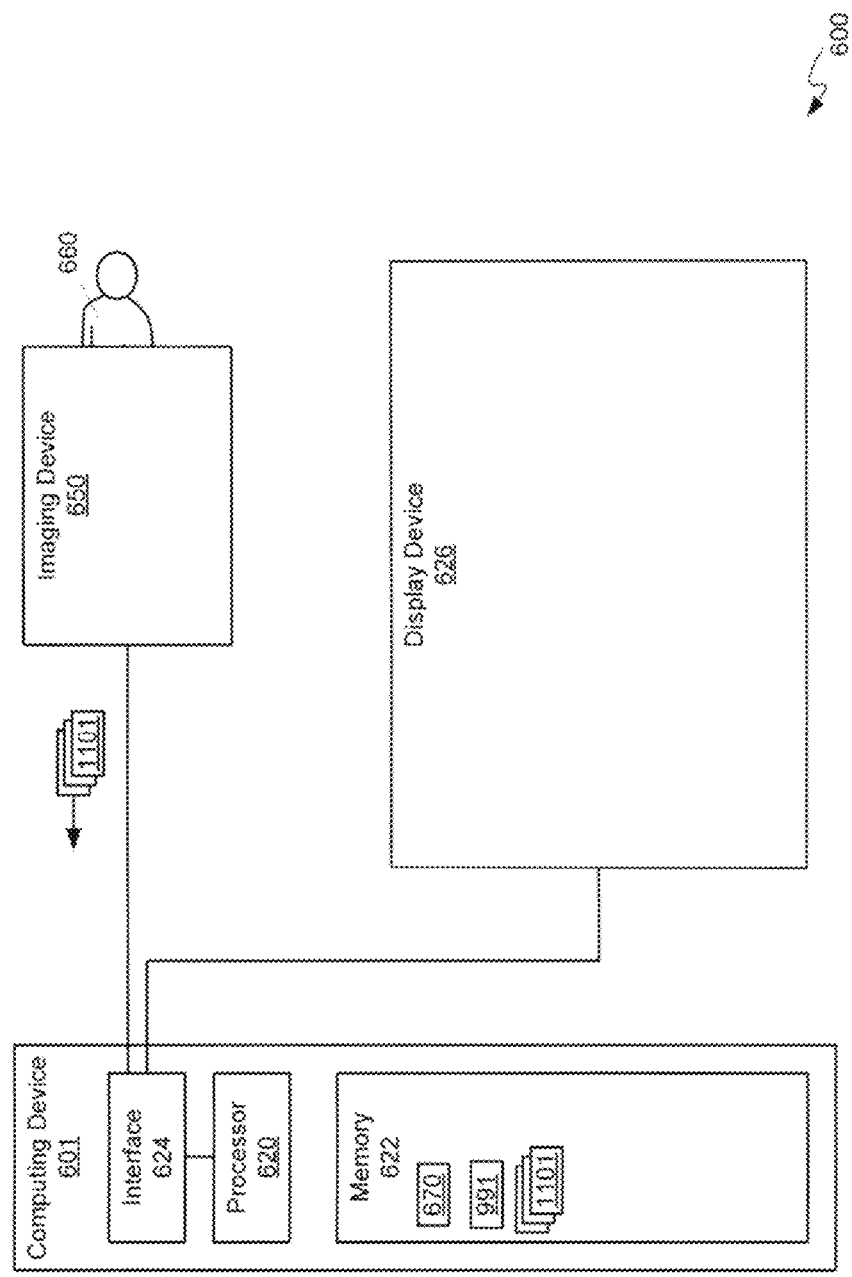
FIG. 11 depicts the system of FIG. 6 when a digital image series is received at a computing device from the imaging device, according to non-limiting implementations.

Attention is next directed to FIG. 11, which is substantially similar to FIG. 9 with like elements having like numbers. In FIG. 11 it is assumed that imaging device 650 has completed the scan associated with first graphical representation 909-1 and transmits a respective digital image series 1101 to computing device 601, respective digital image series 1101 comprising a respective series of digital images acquired during the scan. Processor 620 receives, from imaging device 650, using communication interface 624, respective digital image series 1101 as respective digital image series 1101 is acquired (e.g. block 809 of method 800). While as depicted respective digital image series 1101 is received together (e.g. after all of the digital images in respective digital image series 1101 are acquired), in other implementations, each digital image in respective digital image series 1101 may be transmitted and received as each digital image is acquired. Respective digital image series 1101 is stored at memory 622 (e.g. block 811 of method 800). In general, digital image series 1101 may comprise digital images associated with a scout scan.

Figure 12:
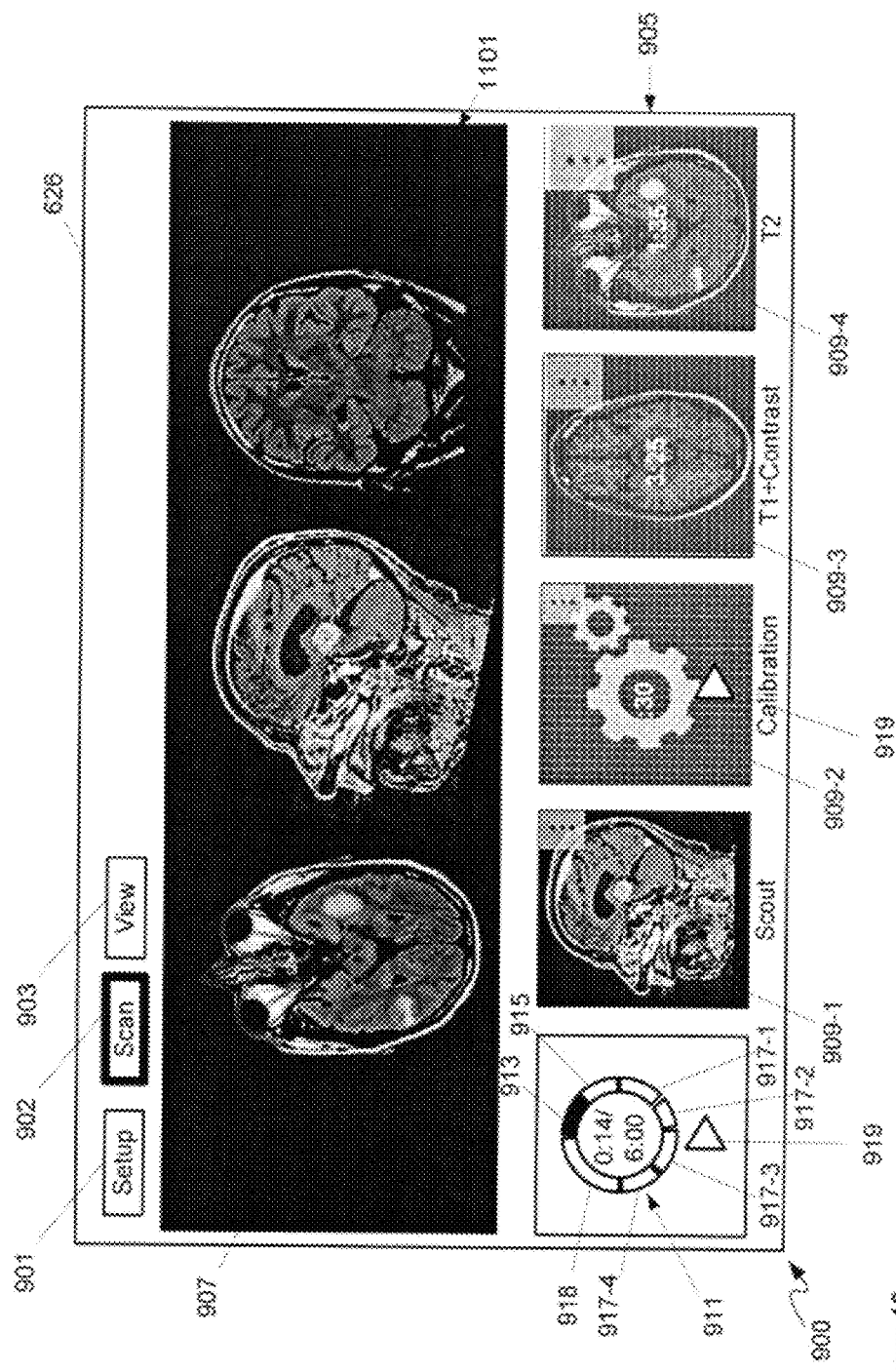
FIG. 12 depicts a third sequence of scan queue management being at least partially implemented using a display device of the system of FIG. 6, according to non-limiting implementations.

Attention is next directed to FIG. 12, which is substantially similar to FIG. 10, with like elements having, like numbers. In general, FIG. 12 sequentially and/or temporally follows FIG. 10, as in FIG. 12 it is assumed that the scan associated with first graphical representation 909-1 has been completed and acquisition of digital image series 1101 has occurred at computing device 601.

In particular, as depicted in FIG. 12, processor 620 is further configured to when acquisition of respective digital image series 1101 has occurred, render, at display device 626, a graphical indicator of a next respective digital image series to be acquired in graphical scan queue 905 (e.g. block 813 of method 800). Many different forms of a graphical indicator of a next respective digital image series to be acquired in graphical scan queue 905 are within the scope of present implementations. As depicted, first graphical representation 909-1 has been optionally rendered to indicate that a scan associated therewith is completed, which inherently indicates that adjacent first graphical representation 909-2 is associated with a next respective digital image series to be acquired in graphical scan queue 905. For example, first graphical representation 909-1 in FIG. 12 is not shaded compared with first graphical representation 909-1 in FIG. 10. However, other sorts of optional shading schemes and/or colour schemes and/or mosaic treatments (e.g. graphical mosaics of respective digital image series 1101) and/or changes to first graphical representation 909-1 may be used to indicate that a scan is occurring. Alternatively, shading schemes and/or colour schemes and/or mosaic treatments may be used to change first graphical representation 909-2 as graphical indicator that first graphical representation 909-2 is associated with a next respective digital image series to be acquired in graphical scan queue 905.

In some implementations, processor 620 is further configured to, when acquisition of respective digital image series 1101 has occurred, render, at display device 626, at first graphical representation 909-1, an animated sequence of respective digital image series 1101 by cycling through at least a portion of the acquisition volume at first graphical representation 909-1; in some of these implementations, the animation includes the entire acquisition volume. Such an animation in the first graphical representation 909-1 may comprise a preview of respective digital image series 1101.

In addition, in FIG. 12, graphical control 1019 has been removed for better clarity, and graphical control 919 has been rendered on first graphical representation 909-2, which inherently comprises another implementation of a graphical indicator of a next respective digital image series to be acquired in graphical scan queue 905. Graphical control 919 also replaces graphical control 1019 in graphical indication 911 of a total estimated time for acquiring the plurality of digital image series. Hence, as depicted, system 600 is paused until one of graphical control 919 is activated as described above, and the presence of graphical control 919 indicates such; however, in other implementations, no pause occurs in the scanning.

As depicted in FIG. 12, processor 620 is further configured to, when acquisition of the respective digital image series 1101 has occurred, render at least a portion of respective digital image series 1101 in information area 907 adjacent graphical scan queue 905. As also depicted in FIG. 12, processor 620 is further configured to, when acquisition of respective digital image series 1101 has occurred, remove the respective graphical timer 1031 from respective first graphical representation 909-1.

Figure 13:
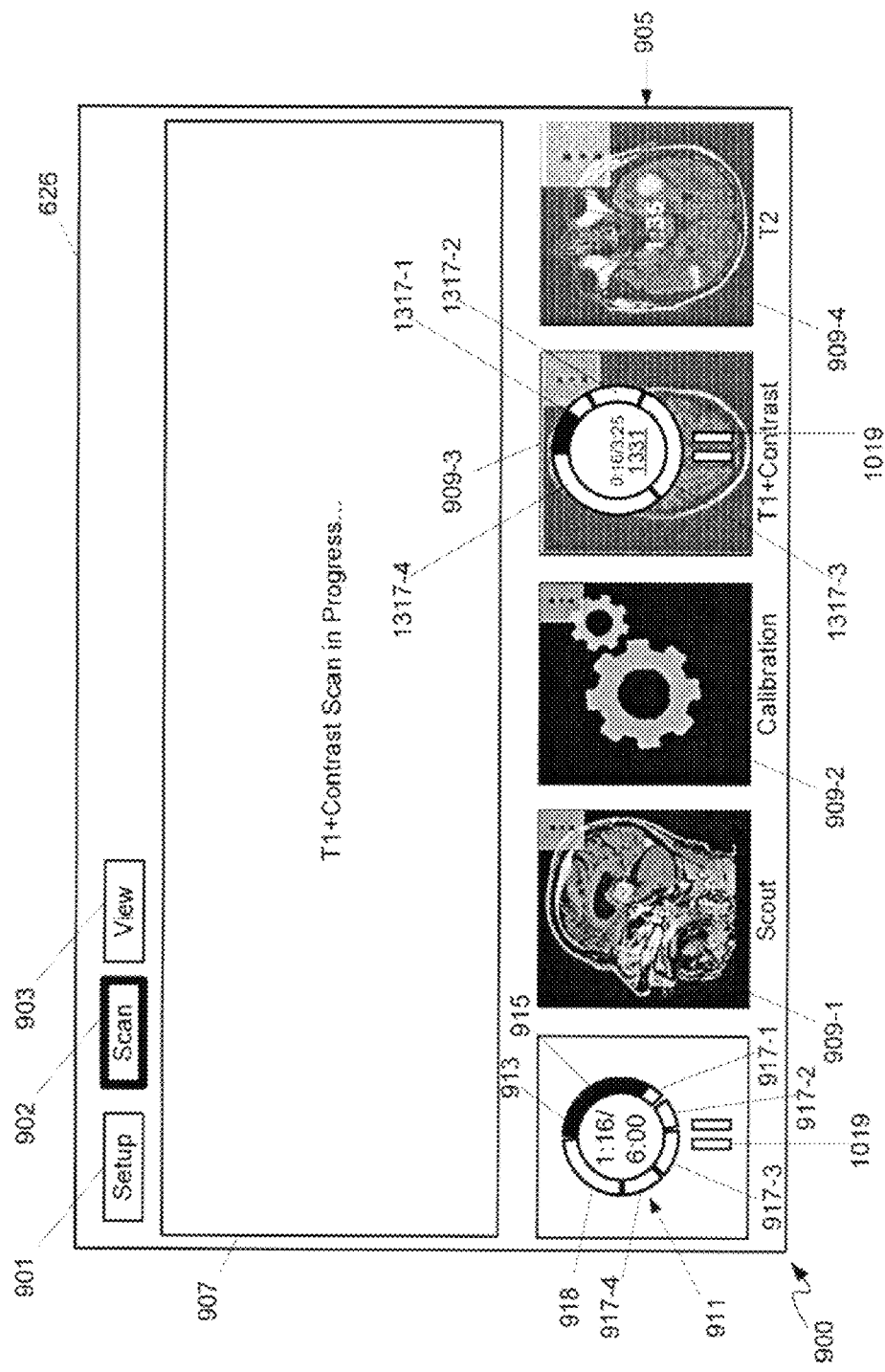
FIG. 13 depicts a fourth sequence of scan queue management being at least partially implemented using a display device of the system of FIG. 6, according to non-limiting implementations.

Attention is next directed to FIG. 13, which is substantially similar in FIGS. 10 and 12 with like elements having like numbers. In general, FIG. 13 sequentially and/or temporally follows FIG. 12 as in FIG. 13 it is assumed that: a scan associated with first graphical representation 909-2 has been completed and acquisition of a digital image series associated with first graphical representation 909-2 has occurred at computing device 601, similar to the acquisition of digital image series 1101. In general, digital image series associated with first graphical representation 909-2 may comprise digital images associated with a calibration scan. Furthermore, first graphical representation 909-2 has been rendered to indicate that the associated scan has occurred and to indicate that a scan associated with first graphical representation 909-3 is next to occur, similar to a rendering of first graphical representation 909-1 in FIG. 12.

In particular, in FIG. 13, a T1+Contrast scan associated with first graphical representation 909-3 is occurring. Such as scan includes a first scan of an area at imaging device 650 in a T1 mode, a pause so that a contrast agent may be injected into the area, and at least a second scan of the area in the T1 mode so that progress of the contrast agent through the area may be determined. As depicted, the T1+Contrast scan associated with first graphical representation 909-3 comprises a first scan, a pause, a second scan and a third scan. Furthermore, a digital image series associated with the T1+Contrast scan in FIG. 13 comprises a first digital image series, a second digital image series and a third digital image series; in other words a digital image series for each scan in the T1+Contrast scan.

As such, a respective graphical timer 1331, similar to respective graphical timer 1031, is rendered on first graphical representation 909-3, but with segments 1317-1, 1317-2, 1317-3, 1317-4 corresponding to each of the first scan, the pause, the second scan and the third scan, (and/or associated with acquisitions of a first digital image series, the pause, a second digital image series, and a third digital image series. Further, segments 1317-1, 1317-2, 1317-3, 1317-4 respectively correspond to segments 917-1, 917-2, 917-3, 917-4 of graphical indication 911 of a total estimated time for acquiring the plurality of digital image series.

As depicted, it is assumed that a first scan associated with first graphical representation 909-3 has been initiated and hence first segment 1317-1 is partially black (indicating time that has passed in the first scan) and partially white (indicating time remaining in the first scan). Similarly, a textual time indication within respective graphical timer 1331 indicates progression in time as a fraction of a total time for all the scans associated with first graphical representation 909-3 (e.g. 0:16/3:25).

Graphical indication 911 of a total estimated time for acquiring the plurality of digital image series is also rendered in FIG. 13 to show progress in the total estimated time for acquiring the plurality of digital image series: the textual timer indicated time progressed as a fraction of total time (e.g. 1:16/6:00), segments 913, 915 are black, indicating that scans associated with those segments have occurred, and segment 917-1 is partially black and partially white indicating that the scan associated therewith is occurring, the relative areas and/or lengths of the black and white areas indicating relative progress of the associated scan. Furthermore, information area 907 is optionally updated to show that a "T1+Contrast Scan is in progress . . . ". However, during a scan, area 907 may be configured to provide any data other than a message that requires and/or requests user action which could result in the scan being interrupted; in these implementations, area 907 may not be updated to indicate a scan in progress.

Figure 14:
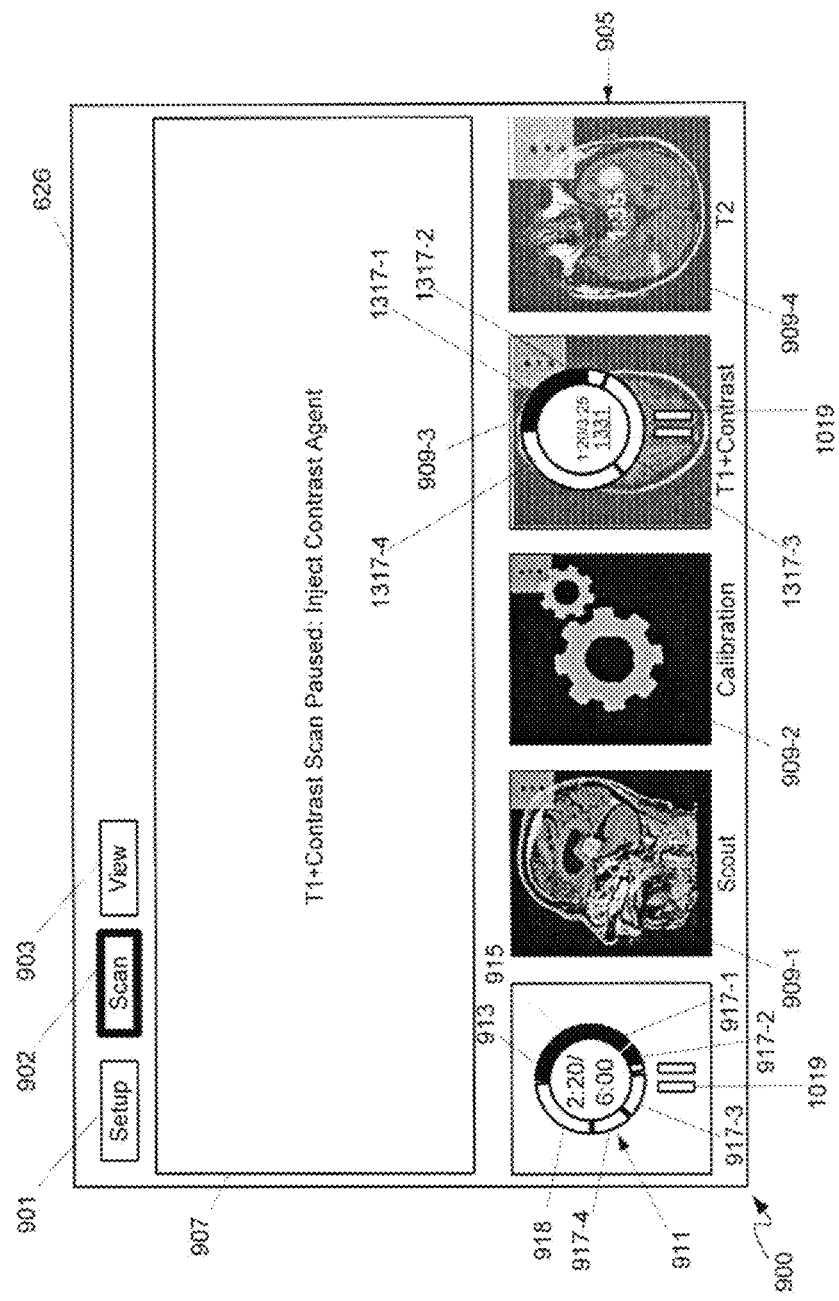
FIG. 14 depicts a fifth sequence of scan queue management being at least partially implemented using a display device of the system of FIG. 6, according to non-limiting implementations.

Attention is next directed to FIG. 14, which is substantially similar to FIG. 13 with like elements having like numbers. In general, FIG. 14 sequentially and/or temporally follows FIG. 13, as in FIG. 13 it is assumed that the scan associated with segment 1317-1 has been completed and processor 620 has automatically paused scanning at imaging device 650. Furthermore, information area 907 has been automatically updated such that instructions for injecting a contrast agent are rendered thereupon and/or to indicate that scanning is paused; in other implementations, such indications may be provided in graphical timer 1331. Progress of time in the pause is indicated in segment 1317-2, as well as in corresponding segment 917-2; in some implementations the time for the pause is predetermined and/or fixed, while in other implementations the time may be adjusted using a menu and the like. Furthermore, as depicted, the pause may be lengthened via actuation of graphical control 1019.

Figure 15:
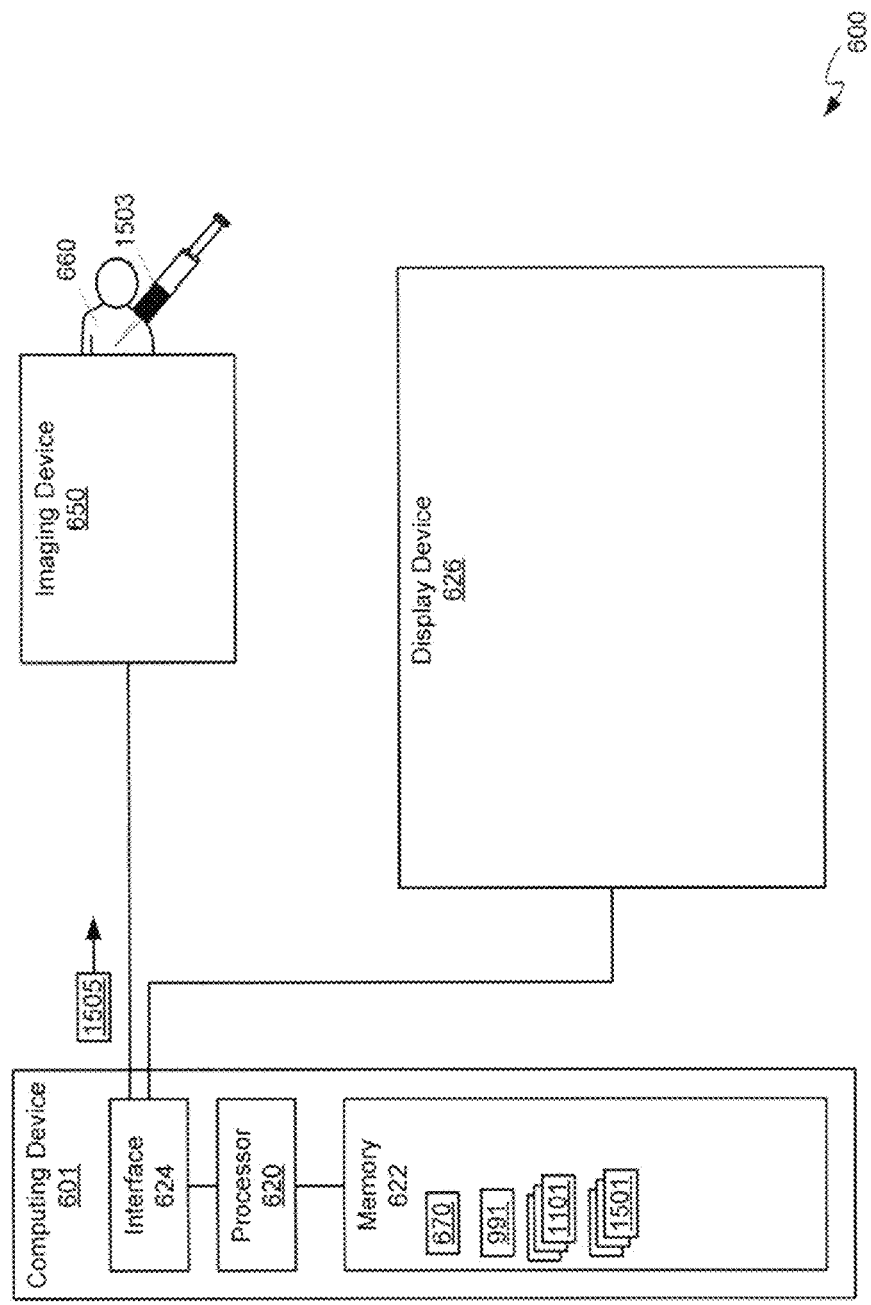
FIG. 15 depicts the system of FIG. 6 when the imaging device is paused for contrast agent injection, according to non-limiting implementations.

As schematically indicated in FIG. 15, which is substantially similar to FIG. 11, with like elements having like numbers, during the pause a contrast agent 1503 is injected into the area of patient 660 being imaged, for example using a syringe and the like. In addition, digital image series 1501 associated with the calibration scan is depicted as being stored in memory 622, assuming that digital image series 1501 was received at computing device 601 in conjunction with a scan associated with first graphical representation 909-2. Furthermore, in FIG. 15, a pause command 1505 is depicted as being transmitted to imaging device 650 from computing device 601, pause command 1505 transmitted when the first scan of the T1+Contrast scan is completed; alternatively, pause command 1505 is not transmitted, but rather such a pause is implemented as instructions in scan prescription 991, and may occur automatically when the first scan is completed; in yet further alternative implementations, pause command 1505 is transmitted when graphical control 1019 is actuated. While not depicted, when pause command 1505 is transmitted, processor 620 is further configured to transmit a scan command when the second scan is to occur.

Figure 16:
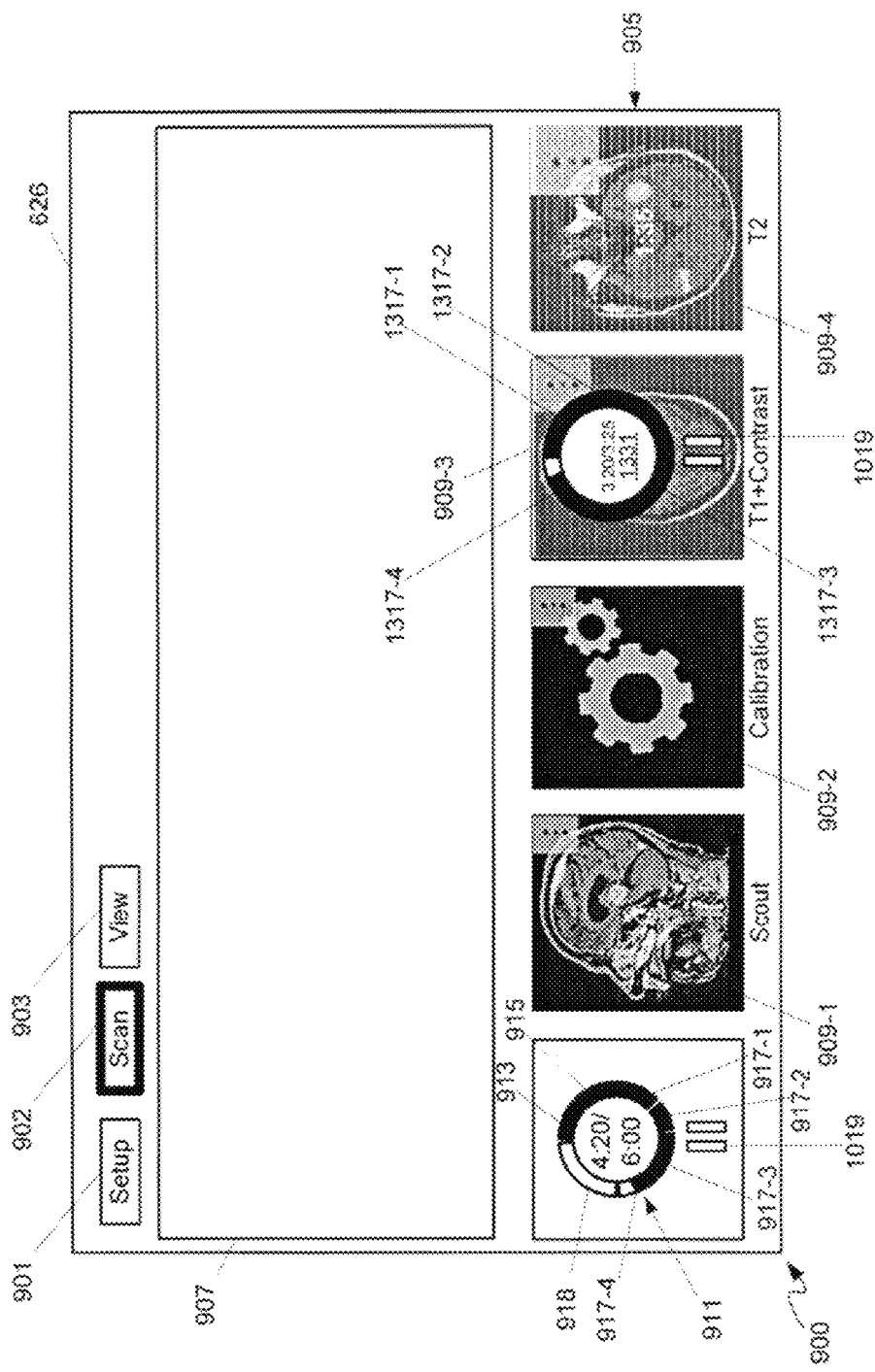
FIG. 16 depicts a fifth sequence of scan queue management being at least partially implemented using a display device of the system of FIG. 6, according to non-limiting implementations.

Attention is next directed to FIG. 16, which is substantially similar to FIG. 14 with like elements having like numbers. In general, FIG. 16 sequentially and/or temporally follows FIG. 14, as in FIG. 14 it is assumed that the contrast agent was injected and that remaining scans associated with segments 1317-3, 1317-4 have occurred and/or are occurring, with both graphical timer 1331 and graphical indication 911 of a total estimated time for acquiring the plurality of digital image series updated accordingly.

Figure 17:
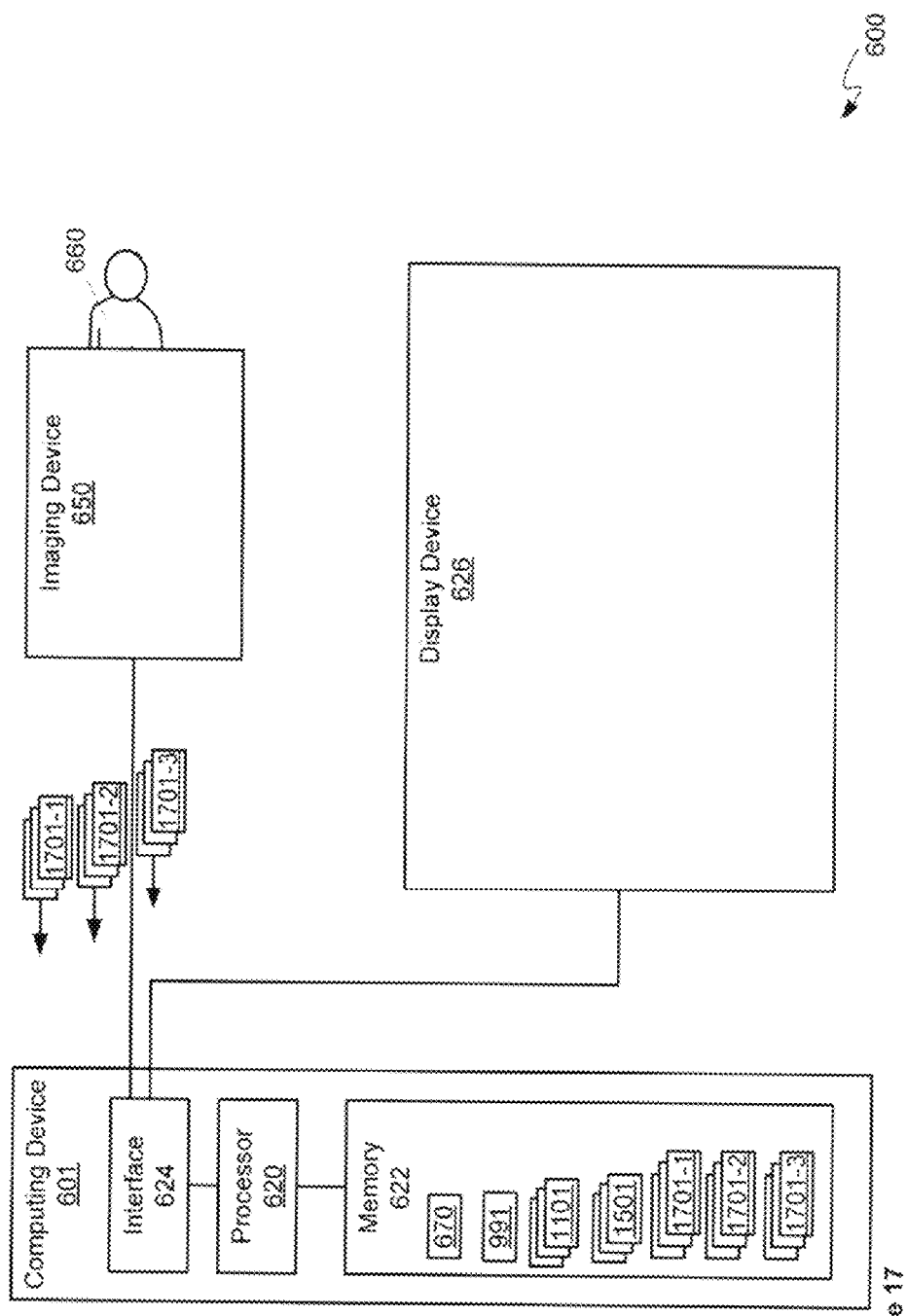
FIG. 17 depicts the system of FIG. 6 when further digital image series are received at a computing device from the imaging device, according to non-limiting implementations.

Attention is next directed to FIG. 17, which is substantially similar to FIG. 11, with like elements having like numbers, where respective digital image series 1701-1, 1701-2, 1701-3 associated with the T1+Contrast scans are depicted as being transmitted to computing device 601 where digital image series 1701-1, 1701-2, 1701-3 are stored in memory 622. Digital image series 1701-1, 1701-2, 1701-3 may be sent as each are acquired, in portions as each image in each digital image series 1701-1, 1701-2, 1701-3 is acquired and/or all at once when all of digital image series 1701-1, 1701-2, 1701-3 are acquired.

Hence, as depicted in FIGS. 13 to 17, in some implementations imaging device 650 is configured to pause when acquiring a respective series of digital images to allow for injection of a contrast agent into an area of patient 660 being imaged, and processor 620 is further configured to insert a pause indication into respective graphical timer 1331 (e.g. adjacent graphical timer 1331, for example, in information area 907, and/or in graphical timer 1331 and/or on first graphical representation 909-3 adjacent graphical timer 1331) corresponding to the pause in acquiring the respective series of digital images.

Figure 18:
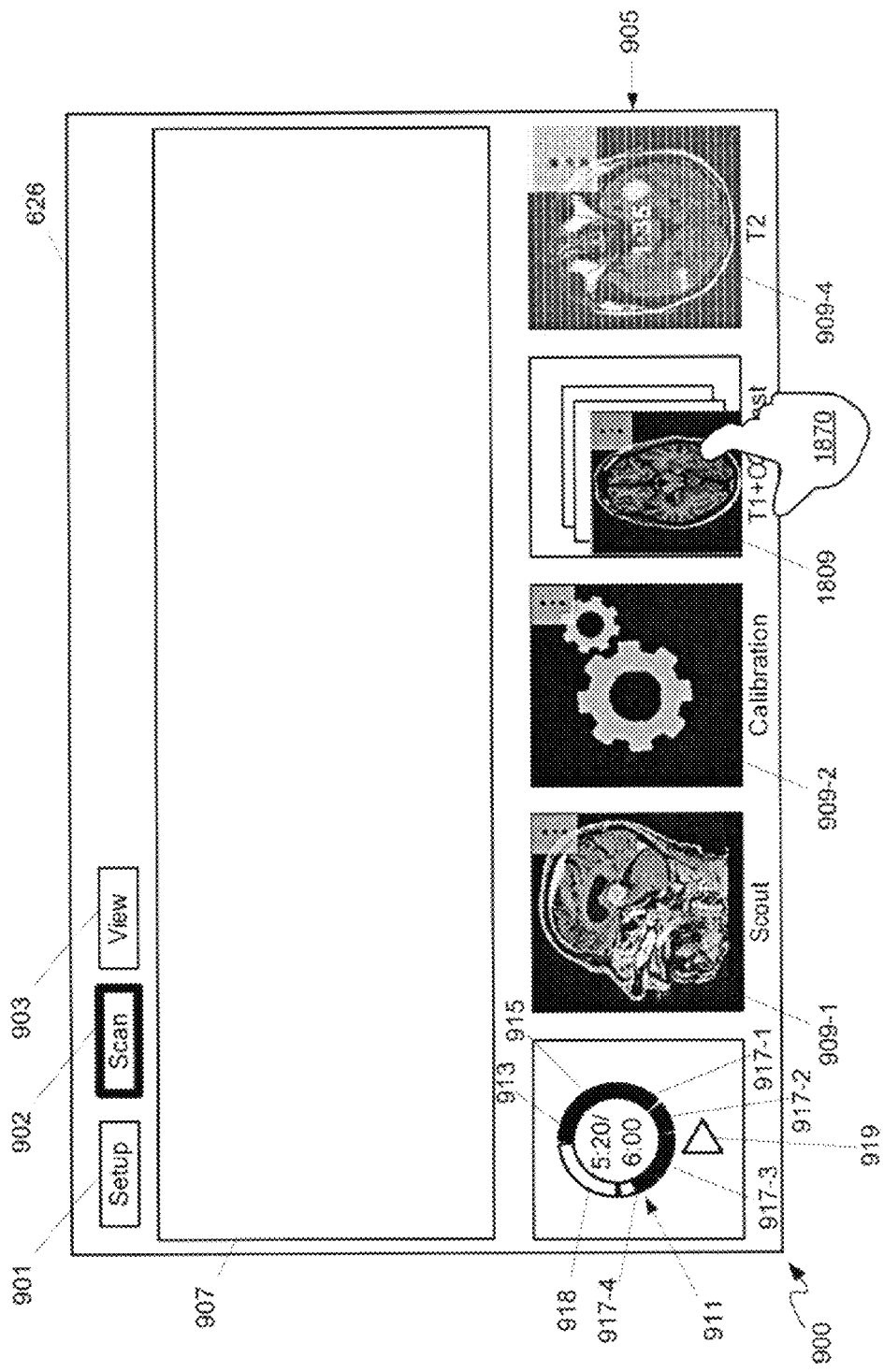
FIG. 18 depicts a sixth sequence of scan queue management being at least partially implemented using a display device of the system of FIG. 6, according to non-limiting implementations.
Figure 19:
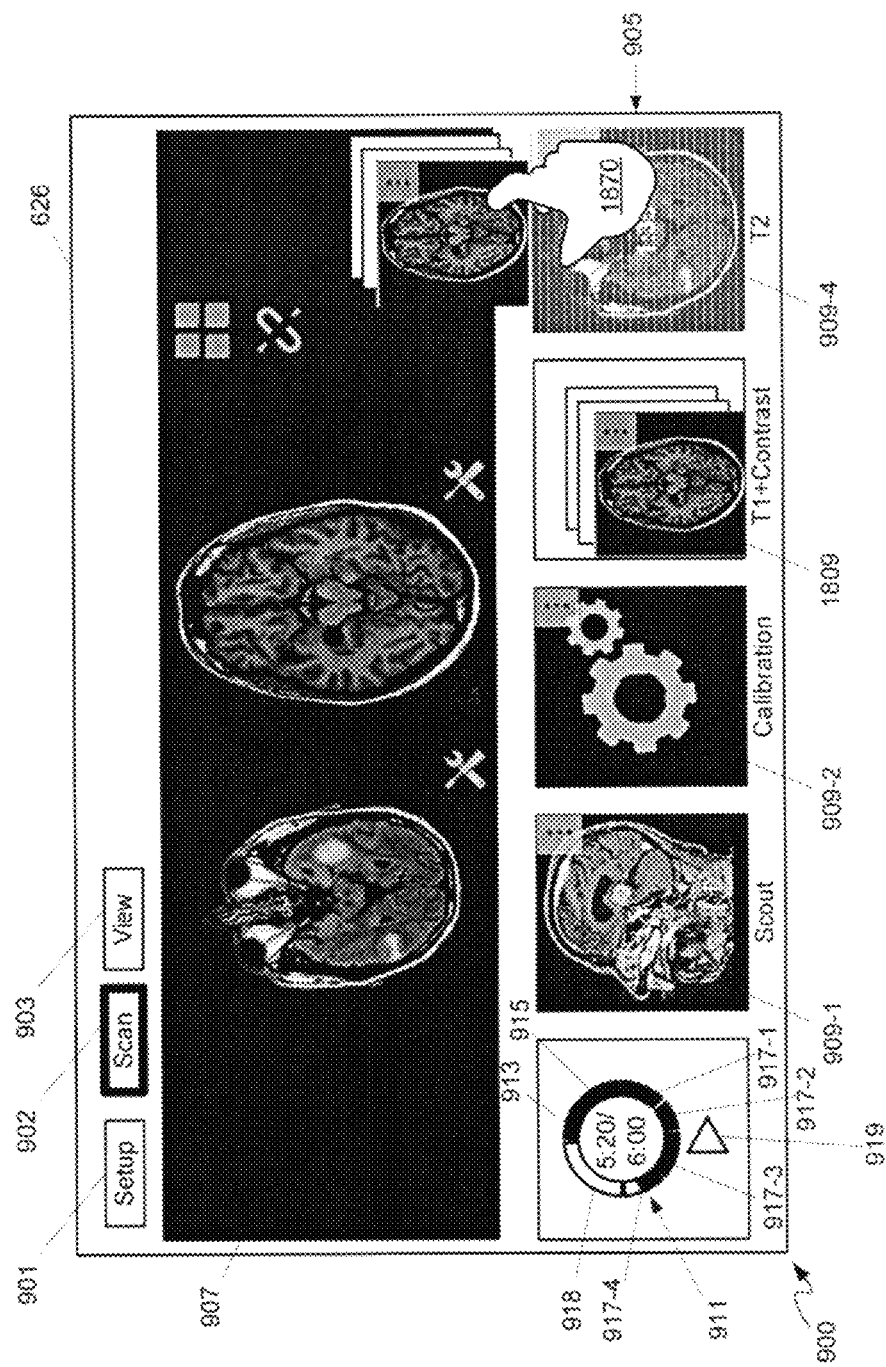
FIG. 19 depicts a seventh sequence of scan queue management being at least partially implemented using a display device of the system of FIG. 6, according to non-limiting implementations.

Attention is next directed to FIG. 18, which is substantially similar to FIG. 16 with like elements having like numbers. In general, FIG. 18 sequentially and/or temporally follows FIG. 16, as in FIG. 16 it is assumed that digital image series 1701-1, 1701-2, 1701-3; it is also assumed for illustrative purposes that system 600 is paused, for example upon actuation of graphical control 1019 and/or when a pause is automatically inserted between scans associated with different first graphical representations 909.

However, in FIG. 18, first graphical representation 909-4 has been replaced with an updated graphical representation 1809 indicative of respective digital images series 1701-1, 1701-2, 1701-3 that was acquired in association with first graphical representation 909-4. In other words, processor 620 may be further configured to, when acquisition of the respective digital image series 1701-1, 1701-2, 1701-3 has occurred, replace first graphical representation 1809 in graphical scan queue 905 with updated graphical representation 1809 indicative of the respective digital image series 1701-1, 1701-2, 1701-3 that was acquired. Such replacing of a first graphical representation 909 may occur for any of first graphical representations and not only when a plurality of respective digital image series are acquired. In other words, as a plurality of respective digital image series 1701-1, 1701-2, 1701-3 were acquired, updated graphical representation 1809 comprises a representation of a plurality of series (e.g. including, but not limited to, a plurality of stacked rectangles and the like, as depicted); as depicted updated graphical representation 1809 comprises one or more digital images from one or more of digital image series 1701-1, 1701-2, 1701-3.

Also depicted in FIG. 18 is a hand 1870 of a user interacting with the touchscreen of display device 626. In particular, as depicted, processor 620 may implement drag-and-drop functionality in that when hand 1870 touches and "drags" updated graphical representation 1809 to information area 907, one or more of the digital images from digital image series 1701-1, 1701-2, 1701-3 is rendered at display device 626 in information area 907. Such images in information area 907 may be manipulated using displayed icons and/or touchscreen techniques.

While not depicted, it is assumed that scanning may resume to acquire digital images associated with first graphical representation 909-4 and/or a T2 scan, in the manner described previously with respect to other first graphical representations 909, with, or without, contrast agent injection.

Furthermore, once digital image series are acquired, they may be viewed in a view mode, which may be activated when selectable option 903 is selected. In such a view mode first graphical representations 909 and/or graphical representation 1809 may remain rendered at display device 626, and associated digital images rendered in drag-and-drop action similar to that described above with respect to digital image series 1701-1, 1701-2, 1701-3. In implementations where display device 626 does not include a touch screen, heretofore drag-and-drop actions may be implemented using a suitable input device.

The present specification describes a medical imaging system for scan queue management in which a computing device coordinates scanning using an imaging device with rendering of a scan queue at a display device. Graphical indications of each scan in a scan queue are provided in an order at the display device which corresponds to a scan order in a scan prescription. The graphical indications are updated as respective scans occur at the imaging device to show an indication of type of scan before a scan occurs, a timer for a respective scan as the scan is occurring and, optionally, an indication of digital images acquired during the scan after the scan has occurred. The graphical indications are provided in conjunction with a timer showing a total time for implementing the scan prescription, in addition to the individual timers for each of the scans. When a scan that is occurring includes a pause for contrast agent injection, the associated timer for the graphical indication is configured to show the pause. The specific embodiments described above have been shown by way of example, and it should be understood that these embodiments may be susceptible to various modification and alternative forms. It should be further understood that the claims are not intended to be limited to the particular forms disclosed, but rather to cover all modifications, equivalents, and alternatives falling within the spirit and scope of this disclosure. In general, such implementations lead to more efficient operation of one or more of the medical morning system and the imaging device, as compared to prior art devices that are primarily text based in their operation. For example, clock cycles for implementing the scanning may be reduced as operation of the present imaging system may be easier than a text based system. Furthermore, total time for imaging may be reduced as a patient may spend less time in the scanning process as an operator of the present imaging system may spend less time in setting up the imaging and less time in implementing the imaging, including the pause for contrast agent injection. In addition, such reduction in set up time may lead to a reduction in user and/or operator error, which may lead to better patient safety; for example, any repeated contrast enhanced scan due to erroneous injection timing increases the toxicity burden of the contrast agent on a patient. As scheduling of medical imaging may place a strain on healthcare systems that depend on medical imaging, such strains may be reduced using present implementations as more patients per day may undergo medical imaging using present implementations. In addition, present implementations may increase an imaging efficiency as confusion of scan queue status is reduced, in present implementations, it may be easier to discern when a series scan has started, paused but later restarted and or when a series protocol is currently undergoing scanning process or editing process.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A medical imaging system for scan queue management, the medical imaging system comprising:
   a computing device comprising a processor, a communication interface and a memory;
   a display device; and,
   an imaging device configured to acquire digital images, the computing device configured to communicate with the display device and the imaging device using the communication interface, communication with the imaging device occurring for a duration of a scan queue series, the processor configured to:
   generate a scan prescription comprising instructions for causing the imaging device to acquire a plurality of digital image series, each of the plurality of digital image series comprising a respective series of digital images;
   render, at the display device: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series;

transmit, using the communication interface, the scan prescription to the imaging device to control the imaging device to acquire the plurality of digital image series;

render, at the display device, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated;

receive, from the imaging device, using the communication interface, the respective digital image series as the respective digital image series are acquired;

store, at the memory, the respective digital image series; and, when acquisition of the respective digital image series has occurred, render, at the display device, a graphical indicator of a next respective digital image series to be acquired in the graphical scan queue, wherein the imaging device is configured to pause when acquiring the respective series of digital images to allow for injection of a contrast agent into an area being imaged, and the processor is further configured to insert a pause indication into the respective graphical timer corresponding to the pause in acquiring the respective series of digital images.

2. The medical imaging system of claim 1, wherein the processor is further configured to, when acquisition of the respective digital image series has occurred, replace the first graphical representation in the graphical scan queue with an updated graphical representation indicative of the respective digital image series that was acquired.

3. The medical imaging system of claim 1, wherein the processor is further configured to, when acquisition of the respective digital image series has occurred, remove the respective graphical timer from the respective first graphical representation.

4. The medical imaging system of claim 1, wherein the processor is further configured to, render, at the display device, estimated times to acquire the respective graphical image series on each of respective first graphical representations prior to each of the respective digital image series being acquired.

5. The medical imaging system of claim 1, wherein the processor is further configured to, when acquisition of the respective digital image series has occurred, render at least a portion of the respective digital image series in an information area adjacent the graphical scan queue.

6. The medical imaging system of claim 1, wherein the processor is further configured to: render, at the display device, an information area adjacent the graphical scan queue: and render contextual operational information in the information area according to a mode in which the medical imaging system is currently operating.

7. The medical imaging system of claim 1, wherein the processor is further configured to control the computing device and the imaging device to operate in one or more modes, the one or more modes including one or more of: a setup mode wherein the scan prescription is generated; a scan mode wherein the plurality of digital image series is acquired; and a view mode wherein the plurality of digital image series are rendered at the display device.

8. The medical imaging system of claim 1, wherein the processor is further configured to render each respective first graphical representation rendered in the graphical scan queue in an order by rendering each respective first graphical representation rendered in the graphical scan queue side-by-side with each other.

9. The medical imaging system of claim 1, wherein the first graphical representation comprises a textual indication of a type of scan associated with an operational mode of the imaging device when acquiring the respective digital image series.

10. The medical imaging system of claim 1, wherein the imaging device comprises a magnetic resonance imaging (MRI) device.

11. The medical imaging system of claim 1, wherein the imaging device comprises one or more of: a magnetic resonance imaging (MRI) device, an Optical Coherence Tomography (OCT) device, a computerized tomography (CT) device, a computerized axial tomography (CAT) device, and a positron emission tomography (PET).

12. A method for scan queue management comprising:
at a medical imaging system comprising: a computing device comprising a processor, a communication interface and a memory; a display device; and, an imaging device configured to acquire digital images, the computing device configured to communicate with the display device and the imaging device using the communication interface, communication with the imaging device occurring for a duration of a scan queue series:

generating, at the processor, a scan prescription comprising instructions for causing the imaging device to acquire a plurality of digital image series, each of the plurality of digital image series comprising a respective series of digital images;

rendering, at the display device: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series;

transmitting, using the communication interface, the scan prescription to the imaging device to control the imaging device to acquire the plurality of digital image series;

rendering, at the display device, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated;

receiving, from the imaging device, using the communication interface, the respective digital image series as the respective digital image series are acquired;

storing, at the memory, the respective digital image series;

when acquisition of the respective digital image series has occurred, rendering, at the display device, a graphical indicator of a next respective digital image series to be acquired in the graphical scan queue;

pausing, the imaging device, when acquiring the respective series of digital images to allow for injection of a contrast agent into an area being imaged; and inserting, via the processor, a pause indication into the respective graphical timer corresponding to the pause in acquiring the respective series of digital images.

13. A non-transitory computer-readable medium storing a computer program, wherein execution of the computer program is for:

at a medical imaging system comprising: a computing device comprising a processor, a communication interface and a memory; a display device; and, an imaging device configured to acquire digital images, the computing device configured to communicate with the display device and the imaging device using the communication interface, communication with the imaging device occurring for a duration of a scan queue series:

generating, at the processor, a scan prescription comprising instructions for causing the imaging device to acquire a plurality of digital image series, each of the plurality of digital image series comprising a respective series of digital images;

rendering, at the display device: a graphical scan queue comprising a first graphical representation of a type of each respective digital image series of the plurality of digital image series, prior to each of the respective digital image series being acquired, each respective first graphical representation rendered in the graphical scan queue in an order corresponding to an order in which the plurality of digital image series are to be acquired according to the scan prescription; and, a graphical indication of a total estimated time for acquiring the plurality of digital image series, the graphical indication of a total estimated time comprising respective graphical indications of respective total estimated times for acquiring each of the plurality of digital image series;

transmitting, using the communication interface, the scan prescription to the imaging device to control the imaging device to acquire the plurality of digital image series;

rendering, at the display device, a respective graphical timer on each respective first graphical representation as each of the respective digital image series are acquired, the respective graphical timer indicating one or more of a time remaining to acquire the respective digital image series and acquisition progress, the graphical indication of the total estimated time updated as the respective graphical timer is updated;

receiving, from the imaging device, using the communication interface, the respective digital image series as the respective digital image series are acquired;

storing, at the memory, the respective digital image series;

when acquisition of the respective digital image series has occurred, rendering, at the display device, a graphical indicator of a next respective digital image series to be acquired in the graphical scan queue;

pausing, the imaging device, when acquiring the respective series of digital images to allow for injection of a contrast agent into an area being imaged; and inserting, via the processor, a pause indication into the respective graphical timer corresponding to the pause in acquiring the respective series of digital images.

* * * * *